US011036985B2

(12) United States Patent
Cork et al.

(10) Patent No.: US 11,036,985 B2
(45) Date of Patent: Jun. 15, 2021

(54) HEAD MOUNTED DISPLAY DEVICE FOR USE IN A MEDICAL FACILITY

(71) Applicant: Fenwal, Inc., Lake Zurich, IL (US)

(72) Inventors: William Cork, Lake Bluff, IL (US); Brian Case, Lake Villa, IL (US); Kevin Krause, Bartlett, IL (US); Kyungyoon Min, Kildeer, IL (US); Witold Moskal, Park Ridge, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 16/261,637

(22) Filed: Jan. 30, 2019

(65) Prior Publication Data

US 2019/0251354 A1  Aug. 15, 2019

Related U.S. Application Data

(63) Continuation of application No. 15/305,260, filed as application No. PCT/US2015/030602 on May 13, 2015, now Pat. No. 10,235,567.
(Continued)

(51) Int. Cl.
*G06K 9/00* (2006.01)
*G06F 3/16* (2006.01)
(Continued)

(52) U.S. Cl.
CPC ...... *G06K 9/00671* (2013.01); *A61B 1/00039* (2013.01); *A61B 1/00048* (2013.01);
(Continued)

(58) Field of Classification Search
CPC ............ A61B 1/00039; A61B 1/00048; A61B 1/00055; A61B 1/00059;
(Continued)

(56) References Cited

U.S. PATENT DOCUMENTS

| 6,847,336 B1 | 1/2005 | Lemelson et al. |
| 10,188,791 B2 | 1/2019 | Burkholz et al. |

(Continued)

FOREIGN PATENT DOCUMENTS

| EP | 2551784 A1 | 1/2013 | |
| WO | WO-2012033244 A1 * | 3/2012 | ........... A61B 5/0022 |

OTHER PUBLICATIONS

"Experience the future of wearable technology—Philips Healthcare," Internet page printed from http://www.healthcare.philips.com/main/about/future-of-healthcare/ on May 8, 2014.
(Continued)

*Primary Examiner* — Anner N Holder
(74) *Attorney, Agent, or Firm* — Becker Patent Law, LLC

(57) ABSTRACT

A head-mounted display device interfaces with a medical device configured to perform an invasive procedure on a patient. The display device includes a frame for mounting on a person's head, a display, a wireless transceiver configured to communicate with a network, and a processing circuit. The processing circuit is coupled to the frame, the display and the wireless transceiver and receives input data relating to the medical device. The processing circuit retrieves from a memory an instruction relating to the medical device based on the input data and displays the instruction relating to the medical device on the display.

19 Claims, 10 Drawing Sheets

Related U.S. Application Data

(60) Provisional application No. 62/134,658, filed on Mar. 18, 2015, provisional application No. 62/106,296, filed on Jan. 22, 2015, provisional application No. 62/106,300, filed on Jan. 22, 2015, provisional application No. 62/106,312, filed on Jan. 22, 2015, provisional application No. 62/106,317, filed on Jan. 22, 2015, provisional application No. 62/088,093, filed on Dec. 5, 2014, provisional application No. 62/079,628, filed on Nov. 14, 2014, provisional application No. 61/993,446, filed on May 15, 2014.

(51) Int. Cl.
*G02B 27/01* (2006.01)
*G16H 40/63* (2018.01)
*A61B 1/00* (2006.01)
*H04B 1/3827* (2015.01)
*G10L 15/22* (2006.01)

(52) U.S. Cl.
CPC ...... *A61B 1/00055* (2013.01); *G02B 27/0172* (2013.01); *G06F 3/167* (2013.01); *G16H 40/63* (2018.01); *G02B 2027/014* (2013.01); *G02B 2027/0138* (2013.01); *G02B 2027/0141* (2013.01); *G02B 2027/0178* (2013.01); *G10L 2015/223* (2013.01); *H04B 1/385* (2013.01); *H04B 2001/3866* (2013.01)

(58) Field of Classification Search
CPC .. A61B 2017/00221; A61B 2090/0807; A61B 2090/502; A61B 3/113; A61B 5/002; A61B 5/02; A61B 5/6803; A61B 5/742; G02B 2027/0138; G02B 2027/014; G02B 2027/0141; G02B 2027/0178; G02B 27/0172; G02B 27/017; G06F 3/167; G06F 19/00; G06K 9/00671; G10L 2015/223; G16H 40/63; H04B 1/385; H04B 2001/3866
See application file for complete search history.

(56) References Cited

U.S. PATENT DOCUMENTS

| | | | |
|---|---|---|---|
| 10,235,567 B2 | 3/2019 | Cork | |
| 2001/0048892 A1 | 12/2001 | Bainbridge et al. | |
| 2005/0203380 A1* | 9/2005 | Sauer | A61B 34/20 600/417 |
| 2006/0142739 A1 | 6/2006 | Disilestro et al. | |
| 2008/0114226 A1* | 5/2008 | Music | A61B 5/00 600/323 |
| 2008/0300572 A1* | 12/2008 | Rankers | G16H 15/00 604/504 |
| 2009/0112630 A1 | 4/2009 | Collins, Jr. et al. | |
| 2011/0234484 A1* | 9/2011 | Ogawa | A61B 1/00039 345/156 |
| 2011/0238079 A1* | 9/2011 | Hannaford | A61B 34/76 606/130 |
| 2012/0041777 A1 | 2/2012 | Case et al. | |
| 2012/0165685 A1 | 6/2012 | Weasler et al. | |
| 2013/0009993 A1* | 1/2013 | Horseman | G06F 19/3418 345/633 |
| 2013/0050069 A1* | 2/2013 | Ota | G06F 3/011 345/156 |
| 2013/0060602 A1* | 3/2013 | Rupp | G06Q 30/0242 705/7.29 |
| 2013/0093829 A1* | 4/2013 | Rosenblatt | G16H 20/40 348/14.01 |
| 2013/0173287 A1* | 7/2013 | Cashman | G06Q 50/22 705/2 |
| 2013/0198685 A1* | 8/2013 | Bernini | G16H 40/63 715/800 |
| 2013/0208234 A1 | 8/2013 | Lewis | |
| 2013/0325508 A1* | 12/2013 | Johnson | G06F 19/3418 705/3 |
| 2014/0019160 A1 | 1/2014 | Loya et al. | |
| 2014/0081659 A1* | 3/2014 | Nawana | A61B 5/742 705/3 |
| 2014/0139405 A1* | 5/2014 | Ribble | A61G 7/002 345/8 |
| 2014/0198190 A1 | 7/2014 | Okumu | |
| 2014/0222462 A1* | 8/2014 | Shakil | G16H 10/60 705/3 |
| 2014/0242563 A1* | 8/2014 | Smith | G06F 19/3456 434/262 |
| 2014/0243682 A1* | 8/2014 | Bindszus | A61B 5/1135 600/473 |
| 2015/0005732 A1* | 1/2015 | Halbert | A61M 5/16854 604/500 |
| 2015/0033128 A1* | 1/2015 | Curd | A61B 34/25 715/728 |
| 2015/0062157 A1* | 3/2015 | Dragnea | G06T 19/006 345/633 |
| 2015/0088547 A1* | 3/2015 | Balram | G06Q 10/20 705/3 |
| 2015/0187196 A1* | 7/2015 | Blair | G08B 5/36 340/691.6 |
| 2015/0379785 A1* | 12/2015 | Brown, Jr. | G07C 5/08 701/29.1 |
| 2016/0055767 A1* | 2/2016 | Tessier | G09B 23/288 434/267 |
| 2017/0186157 A1 | 6/2017 | Boettger et al. | |

OTHER PUBLICATIONS

"Google Glass technology used at Boston hopsital to treat patients," Internet page printed from http://www.dailymail.co.uk/sciencetech/article2600683/, Dec. 2, 2014, 4 pgs.

"These Smart Glasses Could Make Getting a Shot Less Painful," Internet page printed from http://mashable.com/2013/11/20/these-smart-glasses-can-see-your-veins/ on May 13, 2014.

American Red Cross Visual Inspection Reference Guide, (c) 2006.

Autopheresis-C Plasmapheresis System Service Manual, Baxter Healthcare Corporation, Jun. 1999.

EP Communication in App. No. 15725177.8 dated Oct. 25, 2017, 9 pages.

EP Communication in App. No. 17158920.3 dated Jun. 30, 2017, 7 pages.

International Search Report, PCT/US2015/030602, dated Aug. 27, 2015; 14 pages.

Learning About the Autopheresis-C System, p. 3.10, Jun. 1999.

Non-Final Office Action in U.S. Appl. No. 12/976,765, filed Dec. 22, 2010, dated Oct. 30, 2013. 7 pgs.

Letter accompanying subsequently filed items, EP 15 725 177.8, Feb. 21, 2018, 9 pages.

Letter dated Jan. 22, 2018 in EPA17158920.3 and attachments, 13 pages.

Communication pursuant to Art. 94(3) EPC and Annex, dated Jan. 23, 2019 in EP17158920.3, 7 pages.

Reply to communication from the Examining Division and attachments dated Jun. 20, 2019 in EP17158920.3, 35 pages.

Summons to attend oral proceedings and attachments in EP15725177.8, dated Jun. 8, 2020, 11 pages.

Letter "On the summons to the oral proceedings" and attachments in EP15725177.8, dated Dec. 16, 2020, 29 pages.

Oral Proceedings documents from EP15725177.8, dated Jan. 21, 2021 and Jan. 29, 2021, 75 pages.

* cited by examiner

HEAD MOUNTED DISPLAY DEVICE FOR USE IN A MEDICAL FACILITY

CROSS-REFERENCE TO RELATED APPLICATIONS

This application is a continuation of U.S. application Ser. No. 15/305,260, filed Oct. 19, 2016, which is the National Stage of International Application No. PCT/US2015/030602 filed May 13, 2015 and which claims the benefit of the following U.S. provisional patent applications: U.S. App. No. 61/993,446 filed May 15, 2014, U.S. App. No. 62/106,317 filed Jan. 22, 2015, U.S. App. No. 62/088,093 filed Dec. 5, 2014, U.S. App. No. 62/106,312 filed Jan. 22, 2015, U.S. App. No. 62/134,658 filed Mar. 18, 2015, U.S. App. No. 62/106,300 filed Jan. 22, 2015, U.S. App. No. 62/106,296 filed Jan. 22, 2015 and U.S. App. No. 62/079,628 filed Nov. 14, 2014, all of which are expressly incorporated herein by reference in their entireties.

BACKGROUND

The present application relates generally to head-mounted display devices for use in a medical facility. The present application also relates to the use of head-mounted display devices to interface with medical devices used to perform an invasive medical procedure on a patient.

DETAILED DESCRIPTION OF ILLUSTRATIVE EMBODIMENTS

Figure 1:
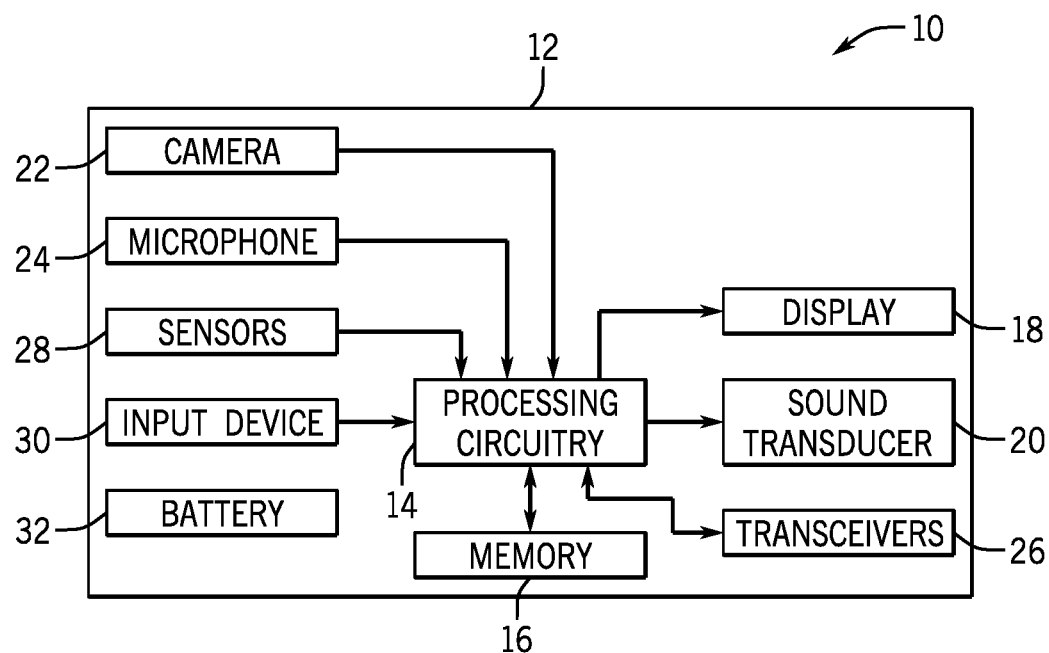
FIG. 1 is a block diagram of an optical head-mounted display device, according to an illustrative embodiment.
Figure 1A:
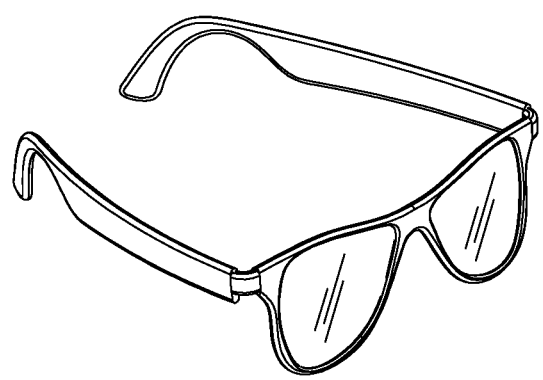
FIG. 1A is a drawing of a frame for a head-mounted display device, according to an illustrative embodiment.

Referring now to FIG. 1, an optical head-mounted display device 10 is illustrated, according to an illustrative embodiment. Device 10 comprises a frame 12 configured to be mounted to a user's head, e.g., comprising a frame configured to hold lenses in front of the eyes. The frame (e.g., FIG. 1A) may comprise one or more of eye wires or rims surrounding and holding the lenses in place, a bridge which connects two eye wires, a top bar above the bridge for structural support, nose pads for resting of the eye wires on the nose, pad arms which connect the eye wires to the nose pads, hinges configured to provide swivel movement, elongated pieces for extending to the ears, curved and/or resilient earpieces for contact with the ears, etc. Embodiments may comprise an elastic headband, helmet, hat, or other components. One or more of the components shown in FIG. 1 may be attachable to a wearable frame 12 or movable to different locations on a wearable housing.

A processing circuit 14 comprises analog and/or digital electrical components configured or programmed to perform any of the functions described herein, including drivers, buffers, amplifiers, etc. Processing circuit 14 may comprise one or more microprocessors, microcontrollers, application-specific integrated circuits, programmable logic devices, etc., which may further be programmed by way of an operating system, applications, and/or other computer programs stored on a tangible memory device. Memory 16 may comprise RAM, Flash, volatile and/or non-volatile memory of a variety of types used to support processing circuit 14 in executing its functionalities.

A display 18 is driven by processing circuit 14 to display data to a user. The display may be disposed directly in front of the eye of the user. The display may be monocular or binocular. Display 18 may be an optical head-mounted display which may be configured to provide images to a user and to allow the user to at least partially see through the display or a portion thereof. Display 18 may comprise a projection display, such as a prism projector, optical waveguide, microdisplay, or other display technology to provide an illusion of an image of an X-inch display at a Y-feet distance, where X and Y are variable depending on the design of the display system.

A sound transducer 20 may be configured to provide audio data output to the user. Sound transducer 20 may be an audio speaker, a bone conduction transducer, or other sound transducer.

A camera 22 is configured to acquire light in the form of images and video and to provide the acquired image data to processing circuit 14. Camera 22 may comprise a forward-facing camera configured to acquire images from in front of the user, a backward-facing camera to acquire images from behind the user, and/or other cameras, such as a camera pointed at the user's eye to detect eye movements or other characteristics of the eye. Acquired images, video, and/or sounds may be stored in memory 16 and/or transmitted via transceiver 26 to a remote device, such as a desktop computer, laptop computer, or smartphone.

Transceiver 26 may comprise one or more wired or wireless transceiver circuits configured to transmit and receive data between device 10 and other computing devices. Transceiver 26 may comprise technology for wide area networks, local area networks, personal area networks, or other networking, such as communications according to a Bluetooth specification, an IEEE 802.11 specification, a Wi-Fi or Wi-Max specification, a cellular specification, a Universal Serial Bus specification, a near-field communication specification, etc.

A microphone 24 is configured to receive audible signals from near device 10 and may be directed and configured to receive spoken commands from a user wearing device 10. Processing circuit 14 may be configured to operate a speech recognition algorithm, such as a natural language processing algorithm, to recognize commands and input given orally by a user wearing device 10.

Sensors 28 may comprise any of a variety of sensor configured to provide input to device 10 regarding the surroundings, movement, location or other characteristics of device 10. Sensors 28 may comprise one or more of an accelerometer, gyroscope, magnetometer, ambient light sensor, proximity sensor, etc.

An input device 30 may comprise other user input devices, such as a push-button input, a touch pad input, a swipe input, hard or soft keys, etc.

A battery 32 may be rechargeable and may provide power needed for mobility of device 10.

In alternative embodiments, any of the teachings herein may be applied to other head-mounted devices, other wearable devices (such as a wrist-wearable device), or other computing devices.

Any of the teachings herein can be applied to a variety of medical devices and procedures. In some cases, these medical procedures may be invasive procedures performed by a medical device suitably configured. Invasive procedures include procedures that penetrate or break the skin or enter a body cavity, such as those that involve a perforation, incision, a catheterization, etc. One invasive procedure is an apheresis procedure performed by an apheresis machine on a patient (e.g., blood donor). Another invasive procedure is an infusion of drugs or other medicants performed by an infusion pump. An infusion may involve intravenous therapy, or the infusion of a liquid substance directly into a person's vein, for such treatments as electrolyte imbalance, to deliver medications, for blood transfusion or replacement, to treat dehydration, etc. Another invasive procedure is an enteral feeding procedure performed by an enteral feeding pump. An enteral feeding pump is configured to pump nutrients at a controlled rate and amount into the nose or abdomen of a person. Another invasive procedure is a parenteral feeding and/or infusion procedure performed by a parenteral feeding pump. A parenteral feeding pump is configured to pump nutrients at a controlled rate and amount in the body in a manner other than through the digestive canal (e.g., through injection).

Certain examples provide mobile applications for medical devices including blood collection or apheresis devices, infusion pumps, drug delivery pumps, and/or other medical devices. For example, an infusion pump infuses fluids, medication, or nutrients into a patient. An infusion pump can be used intravenously, subcutaneously, arterially, and/or epidurally, for example. For example, an infusion pump can administer injections at a variety of rates (e.g., injections too small for an intravenous (IV) drip (e.g., 0.1 mL per hour), injections per minute, injections with repeated boluses, patient-controlled injections up to maximum number per hour, or injections of fluids whose volumes vary by time of day, etc.).

In some infusion pump embodiments, an operator (e.g., a technician, nurse, etc.) provides input regarding type of infusion, mode, and/or other device parameter. For example, continuous infusion provides small pulses of infusion (e.g., between 500 nanoliters and 10 milliliters), with a pulse rate based on a programmed infusion speed. Intermittent infusion alternates between a high infusion rate and a low infusion rate with timing programmable to keep a cannula open, for example. Patient-controlled infusion provides on-demand infusion with a preprogrammed ceiling to avoid patient intoxication. The infusion rate is controlled by a pressure pad or button that can be activated by the patient, for example. Infusion pumps can include large volume pumps (e.g., for nutrient solution delivery to feed a patient), small-volume pumps (e.g., for medicine delivery), etc.

Figure 2:
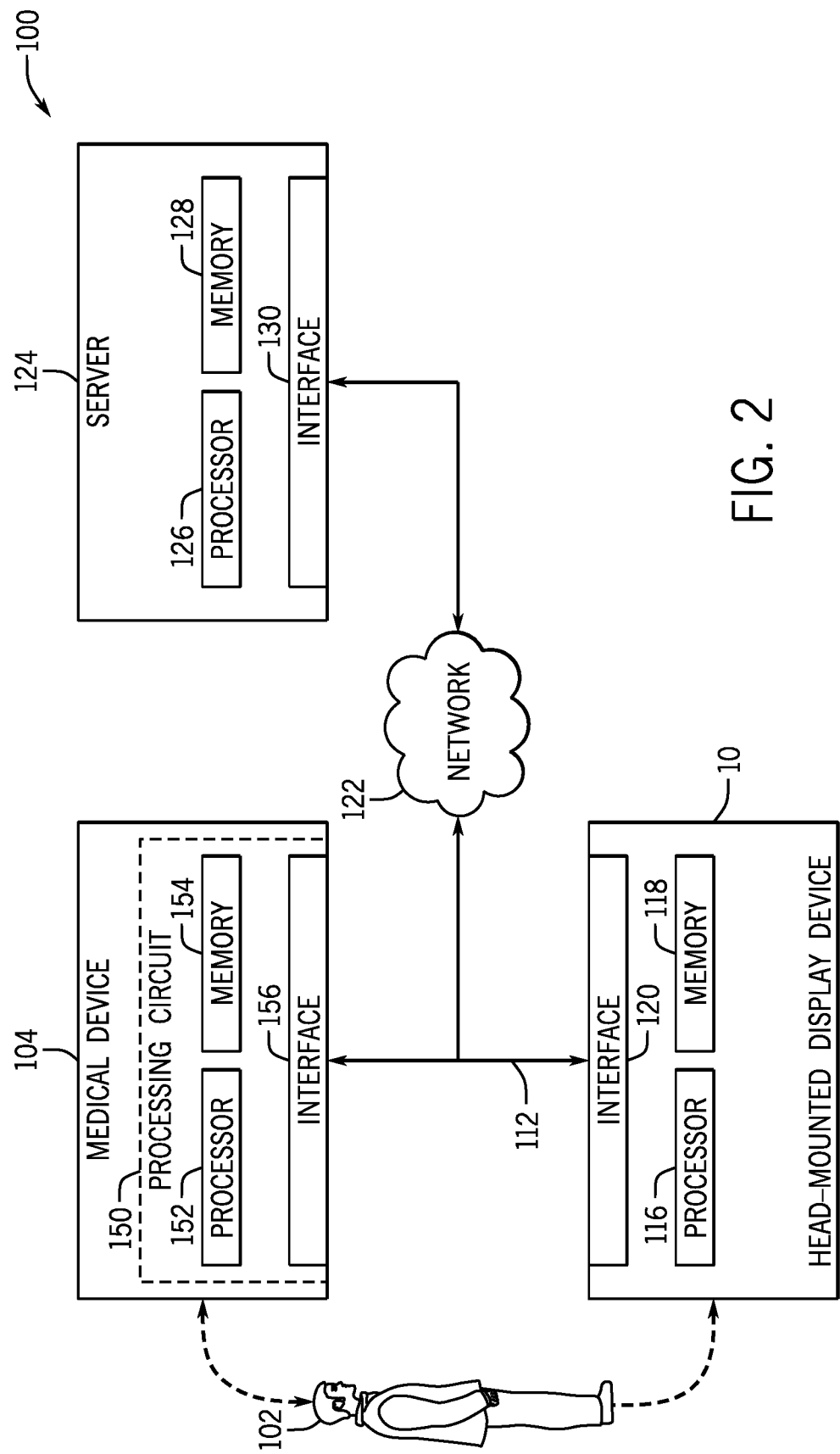
FIG. 2 is a block diagram of a medical facility having a medical device, head-mounted display device and server computer communicating over a network, according to an illustrative embodiment.

Referring to FIG. 2, a medical device 104 may be a device that administers a medicament to subject 102, extracts fluid or tissue from subject 102, implants an object into subject 102, or captures a medical image of subject 102. For example, medical device 104 may be a dialysis machine (e.g., a hemodialysis machine, a hemofiltration machine, etc.), an infusion pump, a drug delivery system, etc. Medical device 104 may be an apheresis machine configured to draw blood from subject 102 (e.g., subject 102 is a donor or receiver of blood components) and/or otherwise process blood components from subject 102. In some implementations, medical device 104 may use measurements taken from subject 102 to control the medical procedure. The measurements may be taken directly by medical device 104 or may be received by medical device 104 via data link or communication link 112 from a measurement device. For example, medical device 104 may use the body temperature, pulse rate, blood pressure, respiratory rate, blood glucose level, pupil dilation, pulse oximetry information, ECG information, or other physical characteristic of subject 102 during the medical procedure.

An optical head-mounted display device 10 may capture or generate data which may be used for record keeping purposes, according to various implementations. For example, device 10 may associate a timestamp with measurements taken from subject 102. Similarly, medical device 104 may associate a timestamp with data received from device 10. In some implementations, server 124 may receive the data from device 10 and/or from medical device 104 and store an electronic record of the reaction of subject 102 to the medical procedure. In some implementations, server 124 may also receive operational data from medical device 104 via network 122. Operational data may include any data indicative of the operational state of medical device 104 during the medical procedure. For example, the operational data may include one or more of a fluid flow rate, a citrate infusion rate, a dosage of substance administered to subject 102 (e.g., a dosage of medicament, saline, blood, blood component, anticoagulant, or other fluid), volume and/or components collected, or other data. In some implementations, the operational data may be time stamped, allowing a record of the operation of medical device 104 to be generated. Medical device 104 may be configured to time stamp the operational data at periodic or intermittent intervals, e.g., at least every 10 minutes, at least every 15 minutes, etc.

Server 124 may be any form of computing device or set of computing devices configured to store and communicate electronic data. For example, server 124 may be a personal computer, a mainframe, a cloud-computing environment, or a data center. Server 124 may include a processing circuit that includes a processor 126 and a memory 128 that stores instructions for processor 126. Server 124 may also include interface circuit 130 configured to communicate with network 122 via a wireless or hardwired connection, according to various implementations.

Network 122 may be any form of computer network that relays information between medical device 104, server 124, and/or a head-mounted device 10. For example, network 122 may include the Internet and/or other types of data networks, such as a local area network (LAN), a wide area network (WAN), a cellular network, satellite network, or other types of data networks. Network 122 may also include any number of intermediary computing devices (e.g., computer, servers, routers, network switches, etc.) that are configured to receive and/or transmit data within network 122.

Server 124 may receive and store data generated by device 10 and/or operational data generated by medical device 104 in memory 128, in some implementations. In further implementations, memory 128 may store information about subject 102 and provide subject data to medical device 104 and/or device 10. For example, subject data may include demographics information about subject 102 (e.g., height, weight, gender, etc.), medical information about subject 102 (e.g., allergies, symptoms, diseases, medical conditions, etc.), or other information that may be provided to other electronic devices by server 124. In some implementations, medical device 104 may adjust its operation based in part on subject data received from server 124. Server 124 may also provide installation data to medical device 104 via network 122 (e.g., to install, update, and/or remove software loaded in memory 154 of medical device 104). Server 124 may be configured to communicate with medical device 104 and/or device 10 via any number of different networking protocols. For example, server 124 may communicate with medical device 104 and/or device 10 via an HTTP connection, FTP connection, SSH connection, a telnet connection, combinations thereof, or other similar networking protocols. In some implementations, server 124 may relay data between medical device 104 and another electronic device. For example, server 124 may be a device that communicates with medical device 104 within the same medical facility and relays information between medical device 104 and a server of the manufacturer of medical device 104 via the Internet.

Figure 3:
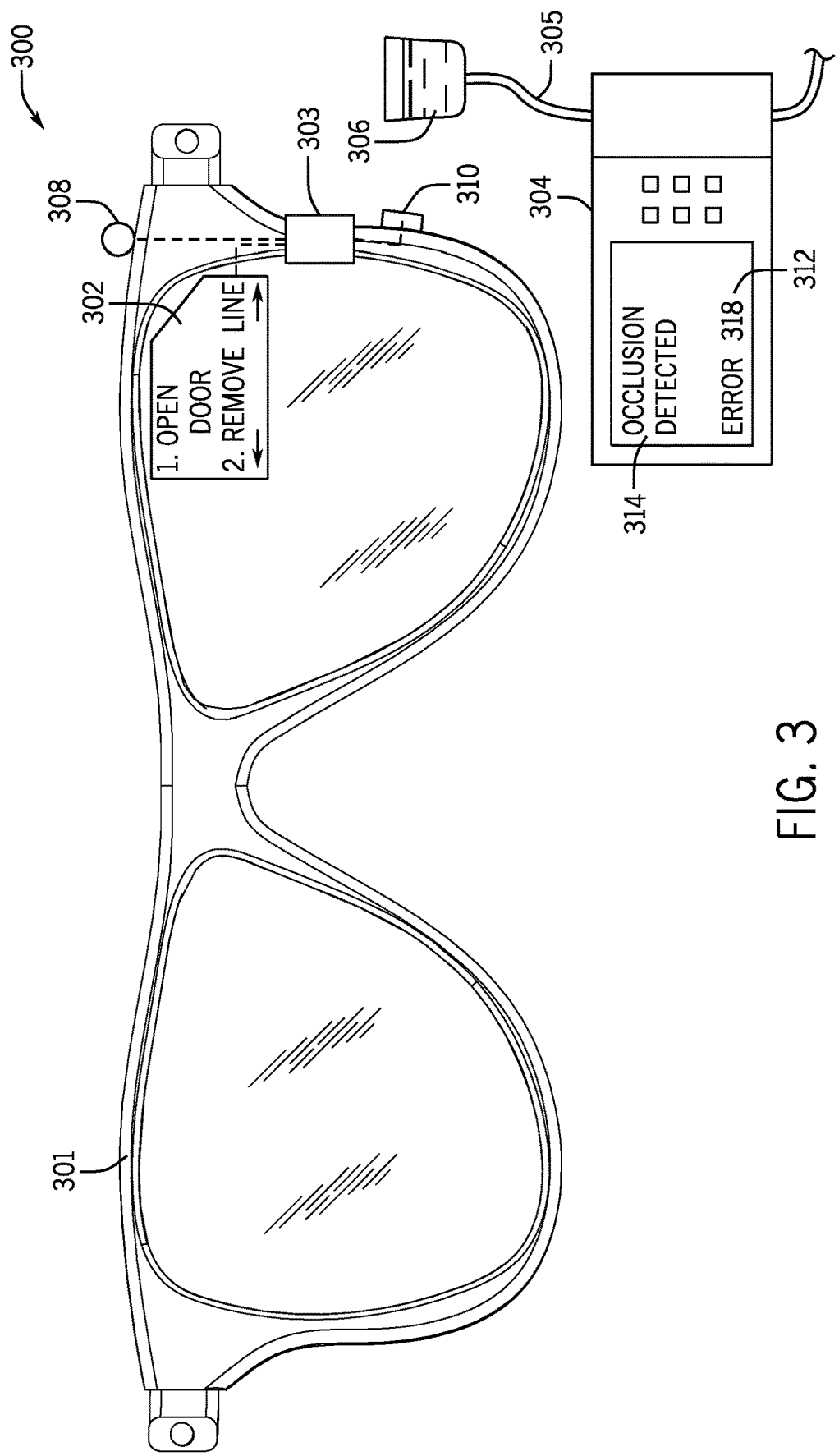
FIG. 3 is an illustration of a head-mounted display for displaying an instruction relating to the medical device, according to illustrative embodiment.

Referring to FIG. 3, a head-mounted display for displaying an instruction relating to the medical device will be described, according to illustrative embodiment. A head-mountable display device 300 has a frame 301 configured to be mounted to a person's head, e.g. as a pair of glasses, a display 302, and one or more other components or features described herein, such as processing circuit 303. Device 304 is a medical device configured to perform an invasive procedure on a patient, in this case an infusion of a medication 306 into a patient (not shown).

In this embodiment, processing circuit 303 is configured to receive input data relating to the medical device. For example, the input data may be a ping or message comprising notification data from device 304 indicating a condition or state of device 304 (e.g., an occlusion has been detected by device 304 in a line or tubing 305.) In another example, the input data may be an image of at least a portion of device 304 acquired by a camera 308 coupled to frame 301 mechanically and to processing circuit 303 electrically. In this example, the camera is configured to acquire an image of medical device 304 in response to user input at a user input device 310 (e.g., a touch pad, a hard key, a soft key, etc.). The user may choose to acquire an image after seeing an error message 312 or other notification 314 on a screen of medical device 304, after hearing an audible alarm, etc. Alternatively, the camera may automatically, without requiring user input, acquire one or more images or video of medical device 304 at periodic or intermittent times, continuously, or in response to a wireless message received from device 304 sent when an alert, alarm or other condition is detected by device 304. Processing circuit 303 may operate a text recognition algorithm (e.g., optical character recognition, etc.) to identify the presence and/or content of a condition of medical device 304 warranting the acquisition of an image or other input data. Processing circuit 303 may be configured to detect a condition of the medical device from an acquired image and to generate the input data used to retrieve the instruction relating to the medical device. For example, from an acquired image, processing circuit 303 may be configured to determine one or more of a make, model or type of medical device, an error code displayed on a screen of device, one or more alert lights being illuminated, a bar code or QR code displayed on the screen, textual messages displayed on the screen, etc. Processing circuit 303 may then generate a request message comprising one or more of these determined data and transmit the request message to a remote computer using its wireless transceiver to request information. Processing circuit 303 may make such a determination by comparing at least a portion of the acquired image with data in a database configured to store information regarding a plurality of different types of medical devices.

Upon visual identification by device 300 of an error, alarm, or other issue, or upon request of a user or receipt of other input data (e.g., from another computer), processing circuit 303 is configured to retrieve from a memory an instruction relating to the medical device based on the input data, and to display the instruction relating to the medical device on display 302. The memory may be local to device 300 or remote (e.g., a server-based memory, cloud-based memory, etc.). The instruction may comprise a plurality of instructions, e.g., step-by-step instructions, displayed and/or heard by a user for procedures, service of the instrument, programming the instrument, entering a test mode of the instrument, responding to alarms, how to program the device, etc. As shown in FIG. 3, the instructions "open door" and/or "remove line" may be provided to a user in response to device 304 detecting an occlusion. The instruction may alternatively comprise a sound relating to the instruction output by a sound transducer of device 300, such as voice instructions to the user.

In one embodiment, the instruction comprises at least three step-by-step instructions, wherein the processing circuit is configured to display each of the at least three step-by-step instructions in a sequence, one after the other, on subsequent screens on display 302. A user may control the display of each screen by pressing input device 310 to move on to the next screen (or back to a previous screen), or using voice commands such as "next screen" or "next instruction" or "complete," which are interpreted by a speech recognition algorithm operated by processing circuit 303.

The instruction may relate to troubleshooting a problem encountered with the medical device, which may comprise one or more instructions to the operator of the device to try different actions with the device to discover and/or solve or address the problem. The instruction may instruct a user how to respond to an alarm or alert generated by the medical device.

In another embodiment, the instruction may be a training instruction configured to train the person how to use the medical device, such as, an introduction to the features and functions of the device, a review of operating instructions, information about new features downloaded to the device by way of a software update, etc. The training instruction may be presented on the display and may further be related to a screen being displayed on the medical device approximately simultaneously, so that information provided to the operator by device 300 and the mode of medical device 304 is at least partially synchronized. For example, a screen may appear on device 304 allowing the operator to begin an infusion. Device 304 may also send a message to device 300 providing an instruction as to which button the user should press to begin the infusion. Processing circuit 303 may further display an icon, such as an arrow, pointing to a button on device 304 to be pushed, as seen through a point of view of the person wearing device 300. Device 303 may direct the user to align their point of view with the screen of device 304 using arrows or audible instructions to direct the person's gaze. Upon detecting that the user's view is suitably aligned, device 303 may provide the icon or other indicator showing the person which button to push. In another embodiment, display 302 may cover substantially all of a lens or both lenses of head-mounted display device 301 and processing circuit 303 may be configured to align indicators on display 302 with areas of device 304, as seen from the perspective of the user of device 301. This alignment may be based at least in part on image data received from camera 308 of device 304. An augmented reality display may be provided using such a system in order to overlay indicators, text, highlighting, etc. over one or more portions of device 304 as seen from a field of view of a user of device 301.

In another embodiment, the instruction may comprise a video configured to train a patient about a procedure to be implemented using the medical device. Device 300 may comprise a sensor (e.g., camera (IR, visible light, ultraviolet light, etc.), microphone, ultrasound sensor, etc.) configured to sense a condition of a patient when the patient is wearing the device, such as the patient's blood pressure, a facial expression, heart rate, etc. Training on medical device 304 can by synchronized with a donor video displayed on display 302. Donor reactions and actions can be synchronized with a training simulation (e.g., what a donor does when an occlusion occurs, when there is low pressure in the device, etc.). Reactions may include the patient closing their eyes, fainting, changing skin color, getting agitated, moving in a certain manner, etc. Processing circuit 303 may use camera 308 to detect and/or record any of these reactions or actions by the patient and to store them and/or analyze them. Any medical device training simulation with a patient may use one or more of these concepts.

In another embodiment, device 300 may comprise a sensor configured to sense a motion or eye position of the person wearing the head-mounted display unit 300 (e.g., a forward-facing or user-facing camera) and to generate control signals for controlling the medical device based on the sensed motion or eye position. Display and/or sounds may be initiated by user motion and/or eye control, as detected by the sensor and processed by processing circuit 303 to generate control messages sent to device 304. In one embodiment, any touch point or input device (e.g., point on a touch screen, hard or soft button, etc.) could be controlled by eye movement/location and a blink to confirm. Device 300 and/or device 304 may comprise imaging hardware or other programmed circuit which records a digital portrait of the user's eye. Using the information about the user's eye, device 300 and/or device 304 may be configured to calculate the approximate location of the user's eye-gaze on a display screen of device 304. Device 300 and/or device 304 may then be configured to execute commands associated with an input device (e.g., menu option, "OK" button, "Back" button, etc.) currently displayed at this screen location. In this way, the user can interact with device 304 by looking at an appropriate sequence of menu options displayed on the screen.

In another embodiment, device 300 and/or device 304 may be configured with a voice processing circuit to receive voice commands for adjusting settings or selecting settings on device 304. The voice processing circuit may be configured with a security feature such as voice recognition which has been taught to the circuit during a training operation, in order to authorize only vocal commands from a certain person or persons. In one example, device 300 is configured with the voice processing circuit, including training, authentication, conversion to commands, etc., though in alternative embodiments, one or more of these functions may be operable on device 304 or distributed between devices 300 and 304.

In various embodiments, portions or all of reference files (e.g., user manuals, service manuals, instructions for use, trouble-shooting guides, community support websites, FAQs, etc.) for procedures, devices, hospitals, blood centers, etc. may be displayed on demand on display 302. Directions or reference materials may be displayed in real time based on a ping from medical device 304. In one example, instructions for use may be provide to assist an operator in setting up a disposable kit. A camera on device 300 may scan a disposable unit installed on the instrument 304 by the operator. A video processing circuit on device 300 may be configured to detect that a clamp on device 304 is closed when it needs to be opened for proper functioning of instrument 304 with the disposable unit. Device 300 may be configured, in response to the detection, to display the color red as an icon, background, or other portion of the display. Device 300 may then be configured to retrieve from a memory a picture or video of the disposable unit/kit properly installed and zoom in on the clamp that needs to be open. The heads-up display could show a GIF (Graphics Interchange Format) file or video file of the clamp being opened, optionally along with textual instructions such as "open this clamp." Additional instructions, such as "try again," "correct," etc. may be displayed in response to an operator's actions with respect to the disposable unit as viewed by the camera of device 300. The screen may provide a green icon, background or other portion of the display, optionally along with a textual message, to indicate the disposable unit is properly installed. In another example, a camera on device 300 may scan a patient before, during or after a procedure is carried out on the patient using device 304. A video processing circuit on device 300 may be configured to detect or notice any of a number of patient conditions, such as any of a number of typical drug allergy symptoms (e.g., skin rash, hives, fever, swelling, watery eyes, etc.). In response, a heads-up display on device 300 may be configured to flash a red color as an icon, background, or other portion of the display. The heads-up display may be configured to display one or more text messages, such as "IMMEDIATE RESPONSE IS REQUIRED!" and/or "DRUG REACTION." The heads-up display may be configured to retrieve from a memory an instruction, such as a text, video, GIF, etc. to assist the operator in how to respond to the symptoms detected, which may include instructions for how to safely shut down the procedure.

Figure 4A:
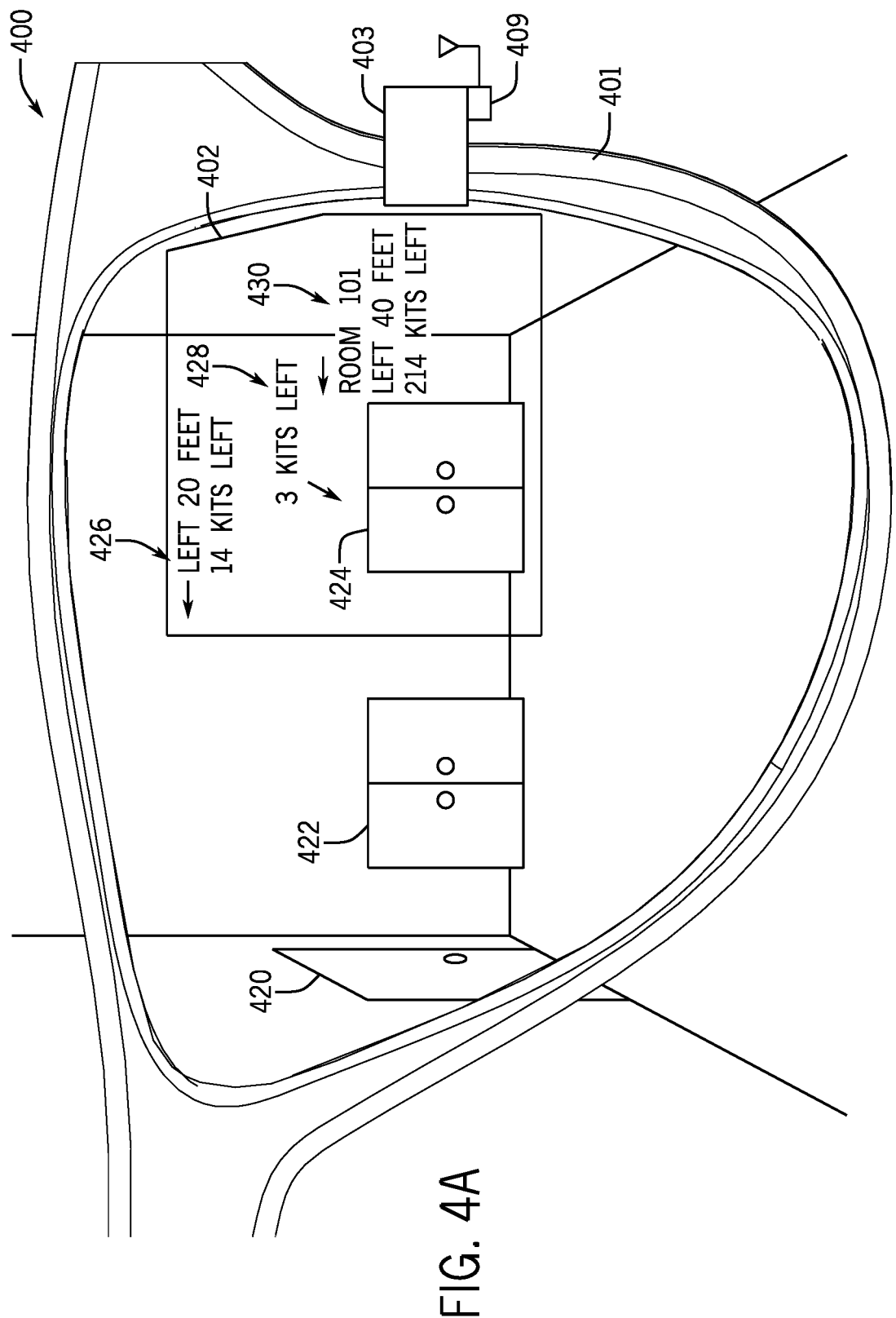
FIG. 4A is an illustration of a head-mounted display for use in a medical facility, according to illustrative embodiment.

Referring to FIG. 4A, a head-mounted display for use in a medical facility will be described, according to illustrative embodiment. In this embodiment, a person wearing the head-mounted display device 400 has a view of the medical facility relative to the frame. Some of the view is through the display 402, while another portion of the view is though a lens of frame 401.

A processing circuit 403 is configured to receive information regarding a location of a medical product or patient in the medical facility via a wireless transceiver 409. For example, the location may be a geolocation (e.g., comprising a latitude, longitude and/or altitude), a room within a building (e.g., Room 101 on the first floor, Room 202 on the second floor), a location within a room (e.g., closet A in Room 101, closet B in Room 101), relative locations (e.g., to your left, to your right, above you, 90 degrees right and 40 meters away, locations using any coordinate system such as Cartesian, polar, cylindrical, etc.), or other locations. The location information may be received from a database remote from device 400, for example an inventory database comprising data regarding instruments, kits, donors, patients, products, disposable components, medical devices, machines, medical supplies, etc., and their respective locations. The inventory database may comprise inventory information about one or more medical device components (e.g., an infusion or enteral feeding pump or component thereof, an apheresis machine or component thereof, a disposable component (e.g., a kit, cassette, tubing, blood transfusion bag, etc.), etc.). The inventory database may comprise one or more server computers accessible via the Internet or another network. The inventory database may be accessible via a direct network connection (wired or wireless) between device 400 and the database.

Additional information, such as quantities, suppliers, SKUs, model numbers, serial numbers, personal information, and/or ID numbers, etc. for the items or people may also be stored in the database. Part or all of the database may be stored in local memory on device 400. The database may be used for inventory control and/or tracking within the medical facility and may be accessible by one or more computers, including device 400. The database may further be configured to provider services for a network of medical instruments, such as backup and recovery data services, remote programming services, software update services, etc. For example, the database may be part of a computer system configured to program different medical devices to operate different blood processing procedures for different patients. The computer system may collect records of blood processing procedures performed for patients on the different blood processing machines and make the records available in report format or for viewing on a separate computer. The computer system may be configured to run diagnostic tests on the blood processing machines in response to an error or in a routine manner.

In FIG. 4A, a room location 420 is shown and two object or shelf locations 422 and 424 are shown. Device 400 is configured to provide a visual indication of the location on the display. FIG. 4 illustrates three examples of visual indications at indicators 426, 428 and 430. These visual indications may be displayed in different regions of display 402, depending on space available, the position of locations within the field of view through display 402 and the position of locations within the field of view of device 400, but outside the field of view of the display 402. The visual indication of the location may comprise a graphical representation in the person's view of the medical facility through the frame and/or in the person's view of the medical facility through display 402. Display 402 may comprise a display surface configured to reflect projected images representing the visual location and to allow the person to see through the display surface into the medical facility.

Upon a person entering a room or requesting information about a medical product (e.g., by speaking to device 400 through a speech recognition engine, by pressing one or more buttons, by selecting from a menu on display 402, etc.), device 400 is configured to retrieve a location of device 400 and a location of the requested items. Location and/or orientation of device 400 may be calculated using a satellite navigation system such as a global positioning receiver, a radio navigation system such as cellular tower triangulation, Wi-Fi location, near field communication (e.g., radio frequency ID) or a position determination entity (PDE), dead reckoning navigation such as use of an accelerometer, gyroscope and/or compass, or other technologies. The location of the requested item may be manually entered into the database by inventory or purchasing personnel. Locations may be determined with any of a wide range of accuracies, such as within 10 meter accuracy, within 1 meter accuracy, an identification of a building, an identification of a room within the building, an identification of a shelf in a room of a building, etc.

Having received the locations of device 400 and the medical products of interest, device 400 is configured to determine how to display indicia of the locations of the medical products of interest. For example, if the medical products are located in another room and outside a field of view of device 400, a textual description or other description of the physical location can be provided, such as indicator 430. Indicator 430 is displayed on display 402 and notifies or instructs a wearer of device 400 that 214 kits of medical product are located in Room 101 (e.g., a physical description) which is to the wearer's left, approximately 40 feet away (namely, room 420). The physical description may represent physical objects or locations, such as room numbers or identifiers, floor numbers, building numbers, a compartment identifiers (such as a shelf, drawer, etc.), a platelet shaker, a freezer location, a particular portable cooler (e.g., if a blood product is coming from a mobile collection), a particular mobile bus number or identifier, etc. Indicator 428 is displayed on display 402 in the vicinity of or near a location where a portion of display 402 overlays a shelf 424 where the kits are located. In this case, an indicator 428 (which may comprise a graphical indicator, such as an indicator having a two-dimensional shape such as an icon or other visual graphic such as an arrow, a flashing light, etc.) is shown immediately adjacent shelf 424 with an arrow pointed toward shelf 424 indicating that 3 kits of medical product are located there. A third indicator 426 instructs the wearer to look 20 feet to the left for another location that has 14 kits of medical product remaining, namely shelf 422, which is within the field of view of device 400 but not overlayed by display 402.

Device 400 is further configured to detect a change in the view of the person and to change the visual indication of the location on the display in response to the detected change in view. For example, as the wearer moves their head to the left to bring shelf 422 within their view through display 402, the indicator 426 may change to an indicator having the characteristics of indicator 428, such as no distance indicator and an arrow pointed directly toward the location. As the view is changed, indicator 426 may be continually updated with a new relative position (e.g., 20 feet, 15 feet, 10 feet, 5 feet, etc.) as the view changes about the room. The processing circuit may be configured to detect the change in view of the person based on at least one of an accelerometer and a gyroscope. A gyroscope can be used to measure speed and/or direction in three-dimensional space. An accelerometer can be used to measure changes in relative position. The processing circuit may be configured to detect the change in view of the person based on a calculated physical location of the device. The processing circuit may be configured to use programmed algorithm techniques, such as perception of perspective and parallax. Using these techniques can give the user realistic depth perception on a display.

In one embodiment, the medical facility is a blood donation facility, wherein the medical product comprises a blood donation kit. A blood donation kit may comprise a blood bag, tubing and/or other components that are configured for use with a single patient (e.g. a blood donor) for a single blood donation and may be considered to be disposable.

Figure 4B:
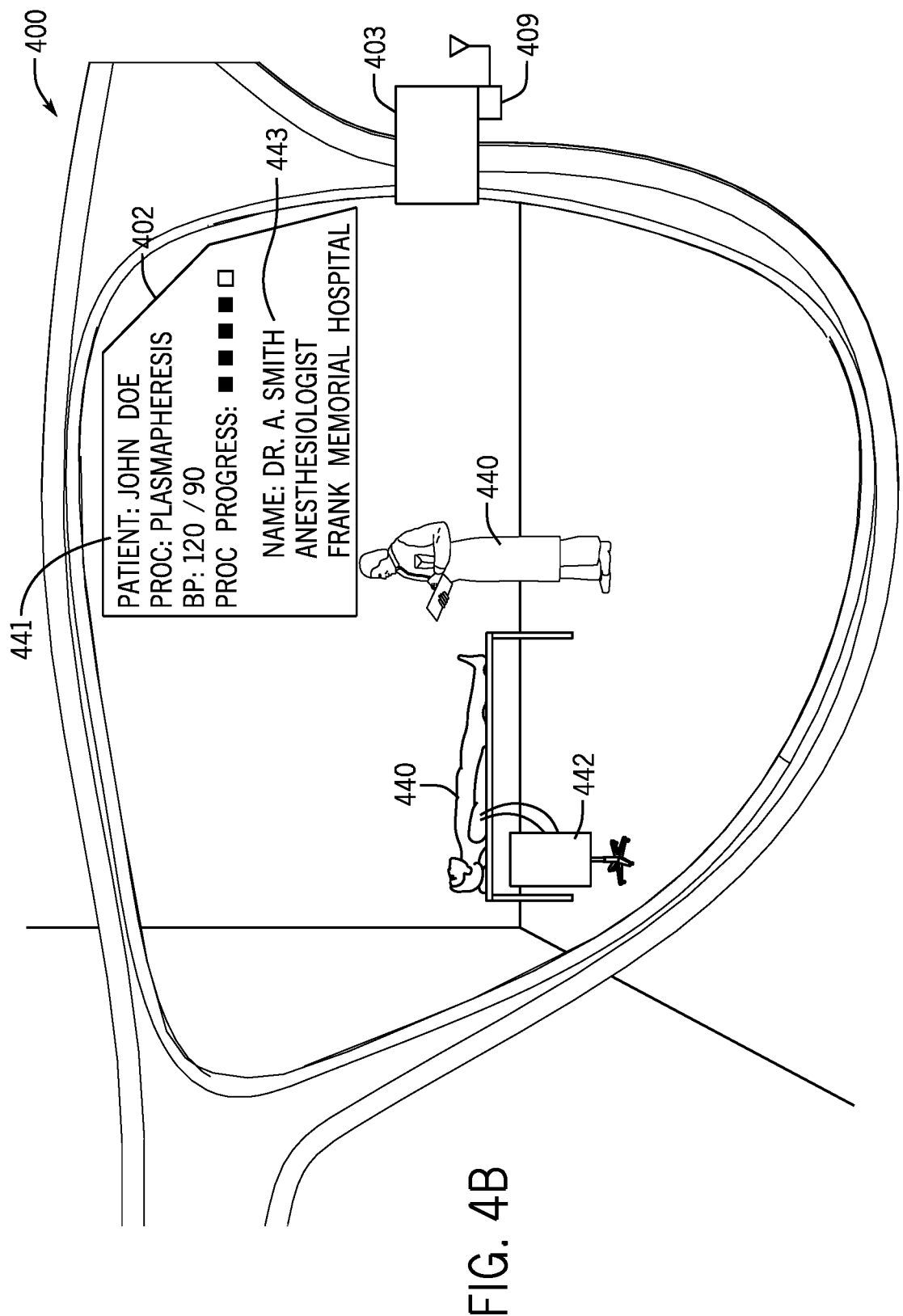
FIG. 4B is an illustration of a head-mounted display for use in a medical facility, according to illustrative embodiment.

Referring now to FIG. 4B, a head-mounted display device for use in a medical facility will be described according to another exemplary embodiment. In this embodiment, display device 400 is configured to receive information regarding a person (e.g., a patient, a healthcare professional, another employee of the medical facility, a patient visitor, etc.). Device 400 is configured to provide a visual indication of information about the person, to detect a change in the view of the wearer of device 400, and to change the visual indication of the information on the display in response to the detected change in view.

Device 400 may be configured to receive information regarding the person within the field of view of the device wearer from any of a number of sources, including sources local to device 400 and sources remote from device 400. For example, information regarding a patient 440 may be received from a hospital management system database which includes records of patients checked into different rooms of the medical facility. Patient 440 may be assumed by device 400 to be the patient that belongs in this room based on the patient record. Further, device 400 may be configured to acquire an image of a portion of patient 440's face and use a facial recognition algorithm to confirm that the face of patient 440 matches data in the patient record (e.g., such as a photograph of the patient acquired at the time of check-in).

Device 400 may be configured to display on display 402 a visual indication 441 of information about patient 440, such as the name of the patient, known allergies, procedure to be performed, last measured blood pressure, progress of procedure (e.g., indicating a percentage or portion complete), etc. The visual indications may be textual or graphical, may use color or flashing indicators to highlight importance of the indications, etc. The visual indications may comprise data acquired in real-time from a medical device 442 monitoring patient 440 and/or a progress of a procedure being performed on patient 440.

Device 400 may further be configured to display visual indications 443 of information about another person in the room 444. Information 443 may comprise an identification of the person (e.g., name, title, role, etc.), an employer of the person, etc. For example, information 443 may indicate that person 440 is a visiting anesthesiologist from a different medical institution. This may be a doctor that the wearer of device 400 is not familiar with. Device 400 may determine the identity of person 440 may acquiring an image of at least a portion of person 440's face or other biometric input, an image of a name tag worn by person 440 using a text recognition algorithm, an input from an RF ID tag or other near-field communication device worn by person 440, or using other techniques. This information may be used to look up further information about person 440 from a local memory or from a server computer for the medical facility comprising data about persons authorized to work in the medical facility. If person 440 is not authorized to work in the medical facility, device 400 may provide a visible and/or audible warning indication to the wearer of device 400. This feature may also be used to confirm that visitors of patient 440 have been previously authorized to visit patient 440 at a check-in process in which an image of the person's face has been acquired, or the person has been giving a near-field communication device for detection by device 400.

In another embodiment, a head-mounted display may be configured to display a list of medical records and/or medical folders to the wearer. A user may request to view medical records by, for example, glaring at a particular item (e.g., a file cabinet, a code printed on a wall, etc.), by using a head tilt to a predetermined direction, by providing a voice request to "View Medical Records," etc. The head-mounted device may then be configured to detect head tilts (e.g., back and forth) to scan through different folders, and then to detect an eye blink or head swipe to view the contents of a folder. Other head, eye, and voice gestures may be used to interact with medical records in other ways, for example, to view, edit, approve, store, save, update, file, select, etc.

Figure 5:
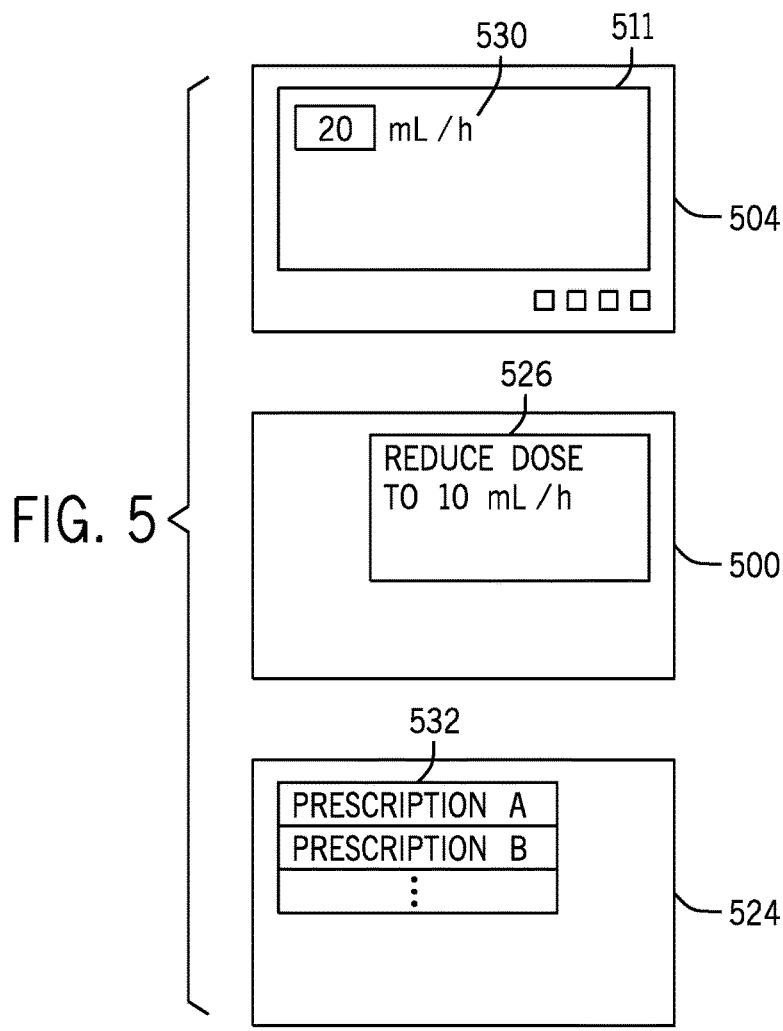
FIG. 5 is a diagram of a head-mounted display device for comparing a characteristic of a medical device with predetermined data for the component, according to an illustrative embodiment.

Referring now to FIG. 5, a head-mounted display device for comparing a characteristic of a medical device with predetermined data for a component of the medical device will be described, with reference to an illustrative diagram. In this embodiment, head-mounted display device 500 is configured to acquire an image of a component of medical device 504 with a camera, to process the image to identify a characteristic of the component, to compare the characteristic to predetermined data for the component, and to generate output data based on the comparison. The output data may be an instruction, alert, warning, verification, screen alert, audible alert, haptic feedback, vibration of device 500, etc. The output data may further trigger or comprise the display of directions on device 500 for correcting information (e.g., programming an apheresis or infusion, etc.). Device 500 may be configured for real time (and/or after data has been entered or the medical device has been programmed) verification of device programming by imaging data displayed on a screen and comparing it to predetermined database information for proper programming, such as a doctor's order or prescription.

In one embodiment, a component of the medical device 504 being imaged is a display 511 coupled to the medical device. The image is processed by a processing circuit of device 500 to determine data programmed into the medical device by the person, wherein the identified characteristic is a programmed value. Indicator 530 shows that a user has programmed the medical device to deliver a medicant to a patient at a rate of 20 milliliters per hour. In this case, device 500 acquires an image of display screen 511 and analyzes the display screen to determine what has been programmed into device 504, e.g., using optical character recognition or other image processing techniques. Device 500 then acquires from a memory 524, such as a prescription database, predetermined data 532, such as prescription data provided by a pharmacist, indicating the correct medical prescription for the patient. Device 500 is configured to generate output data indicating whether the programmed data meets the medical prescription. The output data can be a message, display data, a flag stored in memory, or other data. Device 500 may be configured to provide at least one of an audible and a visual alert in a case where the programmed data does not meet the medical prescription.

Device 500 may further be configured to display an instruction 526 to the person for correcting the programmed data. For example, instruction 526 instructs the wearer of device 500 to reduce the dosage rate to 10 milliliters per hour, in accordance with the prescription data 532.

In one embodiment, device 500 may be configured at a first time to acquire an image of a written prescription, store the information regarding the prescription in memory 524 as prescription data 532, and then later retrieve the prescription data 532 to carry out the comparison described above.

In another embodiment, device 500 may be configured to monitor and track user error corrections, such as when a user erroneously inputs data or information and changes the data/information after inputting it. Device 500 may use this information to alert specific or general users about potential errors in real-time based on previous errors and/or corrections made by the specific user or by the general population of users that are tracked/monitored. The alerts can be at specific steps during data input or can be based on the particular data being entered in the system.

In another embodiment, the component imaged is a disposable component configured to be loaded into the medical device, such as a blood donation kit having tubing and a blood bag and optionally a cartridge. In this embodiment, the characteristic of the disposable component is an indication of how the component is loaded into the medical device and wherein the predetermined data is data representing a proper loading of the component. For example, device 500 may provide kit loading verification (e.g., visual identification to ensure proper loading of kits before a procedure is commenced). For example, one or more codes, marks, or indicators may be printed on the medical device that would be covered by portions of the disposable component (or on the disposable component that would be covered by the medical device) when the component is properly inserted. Device 500 may use its camera to look for those marks and, finding none, conclude that the component is properly installed. Other image processing techniques may be used to identify proper installation of a disposable kit.

Device 500 may also provide counterfeit kit identification and tracking, with information being sent directly to a server computer of a manufacturer of medical device 504 for further analysis. Device 500 may be configured to identify aspects of a disposable kit that are present only on authorized disposable kits or only non-authorized disposable kits that are observable (e.g., using any type of camera, such as visible light, infrared, etc. or ultrasound, RFID, or other sensors). The component may be a disposable component (e.g., a blood donation kit, a transfusion bag, cassette, etc.) configured to be loaded into the medical device, wherein the predetermined data is data indicating a type of disposable component, wherein the comparison indicates whether the disposable component is of a known type. The type may be a model number, serial number, manufacturer, size, capacity, or other type. The predetermined data may represent a type of disposable component approved for use with the medical device, such as approved by a manufacturer of device 504, approved by the medical facility, approved by a biomedical engineer on staff at the medical facility, etc. In this case, the output data may comprise a message indicating the disposable component is not approved for use with the medical device or which has been recalled, which may be displayed on display 526 and/or sent wirelessly to a remote computer.

In another embodiment, medical device 504 may be a blood transfusion device. A blood transfusion bag may be verified by capturing an image of the bag upon removal from a hospital refrigerator, using device 500, and also verified at the point of transfusion. For example, device 500 may be programmed to acquire (e.g., automatically, without requiring user input) an image of the blood transfusion bag when it is in a location in the vicinity of a previously programmed known location, namely, the location of the hospital refrigerator. Device 500 may further use image recognition to identify an object in the camera's field of view that corresponds to the size, shape, or other distinctive features of a blood transfusion bag. The verification may involve matching a patient with the blood bag ordered to verify blood type, patient identifier, or other characteristics. The characteristic may be a code printed on the blood transfusion bag, wherein the predetermined data is data associating the code with a particular patient. The characteristic may alternatively be a date indicative of expiration of blood within the blood transfusion bag, in which device 500 compares the expiration date to the current date and provides an alert to the wearer of device 500 if the expiration date has passed. Bag tagging may occur at the time of blood component donation: after blood component collection, labels are placed on the product that identify the blood type (O+, A−, etc.). The head-mounted display can be used at the time of blood donation to confirm the label to the donor. During usage of the blood, at the time of transfusion, the head-mounted device can check the label on the bag and confirm it is the correct blood product and correct blood type prior to transfusing to a patient. A head-mounted device could also be used during an infusion to check drug type, dose, concentration, etc. by matching labels.

A head-mounted device may be configured to check for various type matching of the blood component(s) by "scanning" the bag (label or RFID tag) and comparing it to patient record data retrieved from a database and/or patient file.

Prior to some surgeries, a patient will donate some of their blood components that will then be given back to them during the surgical procedures (autologous donation). In this or other situations, the patient may go to a blood donation center X weeks prior to the surgery, and an autologous collection takes place (component removal would be based on their specific needs). The blood component collected would be labelled/tagged with the patient's identification. This could be done by storing the information in a bar code or RFID chip. The identification would be a biometric marker, such as a facial profile/feature, voice mapping, retina map, etc. At the time of the surgery, the specific blood component would be "scanned" by the head-mounted-display and then the patient would be verified using the HMD using a biometric marker comparison.

In another embodiment, real-time monitoring of activities of the operator of medical device 504 may be implemented using head-mounted device 500. Monitoring may include identification of incorrect input, loading, use, etc. Device 500 may be pinged (by way of a handshake, gate, or other message) by medical device 504 for regular checks of what device 500 sees through one or more cameras or other sensors. Each check must be confirmed by the operator before medical device 504 will allow the operator to proceed to the next step in a process of setting up the device, or before medical device 504 will allow a procedure on a patient to begin. The person using device 500 may also acquire images or perform checks at their discretion using a user input device (such as a pushbutton, microphone and speech recognition engine responding to a voice command, detected eye movement, etc.). For example, the person may wish to confirm proper loading of the kit, confirm anticoagulant is loaded (vs. saline), etc. at routine intervals during setup or procedures. Similarly, for an infusion, checks may be made for proper drug, volume, flow rate, bolus size, etc. each time a value is programmed, when a new syringe or bag is loaded or connected to the pump, etc.

In another embodiment, medical device 504 may be an infusion pump and device 500 may be configured to confirm that the drug name and/or type, volume to be infused, infusion rate, bolus size, etc. have been correctly entered in the infusion pump before the infusion pump enables the infusion procedure to begin. For example, device 500 may acquire an image of a name of a drug from a label on a drug source (such as a bag, syringe, etc.) holding the drug to be infused. Device 500 may be configured to recognize text on the label. Device 500 may then look for a screen of the medical device 504 and monitor inputs provided to the screen by an operator. When device 500 recognizes that a name of a drug has been selected on the screen, it may compare the name to the name recognized from the drug source. If the names do not match, an alert may be provided. If the names do match, either no alert may be provided, or a positive alert message, such as "CORRECT DRUG ENTERED" may be displayed on a display of device 500 for viewing by a wearer of device 500. A similar check or confirmation may be performed by device 500 each time a new syringe or drug is loaded/connected to the pump.

In another embodiment, the head-mounted device may be configured to recognize a drug's concentration, for example by reading a colored label on bag or syringe of medicament (in a case where a company uses differently-colored labels to distinguish concentration) or by recognizing the specific drug concentration using image processing techniques such as color matching, optical character recognition, etc.

As mentioned, the image may be acquired by device 500 in response to a message received from the medical device, for example to verify the bag before or after it is installed in the medical device 504. The message may be received by direct wireless communication between the head-mounted display device and the medical device (e.g., without an intervening separate computer) or by communication between a remote server computer and the head-mounted display device (e.g., through a plurality of communication networks).

In one embodiment, the processing circuit is configured to receive at least two messages configured to trigger the acquisition of the image at different times during preparation or operation of the medical device, for example intermittently, or at different stages in programming device 504.

In various embodiments, the component of the medical device being scanned, imaged, or viewed by device 500 may be a display, an input device (e.g., a knob, button, switch, lever, soft key, hard key, etc.), a disposable component used in a medical procedure, a replaceable component, a battery, a mounting mechanism, a tubing, a source of a drug, a blood component receptacle or bag, a cartridge, a door locking lever or mechanism, a warning or messaging light, or other components of various medical devices. In other embodiments, the component of the medical device being scanned may be a clamp to indicate whether the clamp has been opened or closed by a user, an installation of colored tubing into the correct colored clamp or colored pump, correct spiking of a bag (e.g., a red spike on a tube matches a red bag of medicament or nutrition source), correct tube in the air detector, using tube size or geometry of tubing loop, correct tubing placed in a sensor on the instrument, etc. The head-mounted device could also be configured to count the number of drops from a solution bag into a drip chamber of a transfer set to ensure the proper flow rate is being achieved (for example if no pump is used and the clinician is instead doing a gravity drain).

In various embodiments, the characteristic of the component of the medical device being scanned, imaged or viewed by device 500 may be any text printed on the component, a color of the component, information displayed by the component, a condition of the component (e.g., is the bag full, empty or partially empty, is the component damaged or in working condition, is the component packaged or ready to use, is the component tightened or loosened, etc.), a position of the component relative to the medical device (e.g., installed or not installed, covering an indicator on a medical device or not covering the indicator, etc.), a setting of the component (e.g., on/off, a value the component is set at, etc.), or other characteristics of the component.

Figure 6:
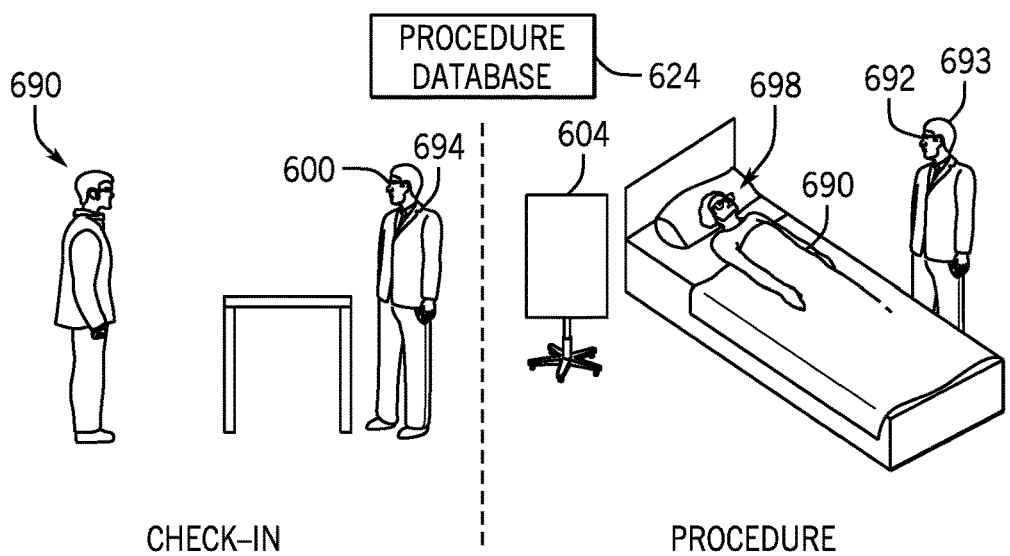
FIG. 6 is an illustration of a head-mounted display device for a patient identity check, according to an illustrative embodiment.

Referring now to FIG. 6, a head-mounted display device for a patient identity check will be described, according to an illustrative embodiment. In this embodiment, a head-mounted display device may be used to verify the identity of a person in a medical facility or clinical setting. The device may be worn by a patient (e.g., blood donor, surgical patient, etc.) or by a clinician (e.g., doctor, nurse, administrative staff, etc.) and the identity check may be based on facial recognition and/or saying a person's name at check-in or at the time of the procedure (e.g., donation, surgery, etc.). The patient could be observed by glasses worn by the clinician and/or the patient could put the glasses on to be identified.

In one embodiment, device 600 is configured to receive at least one of sound and image data from a sensor (e.g., a microphone configured to sample a voice of the patient, a camera configured to acquire an image and recognize a face and/or body of the patient, etc.). The sound and/or image data are associated with a person in the vicinity of the device, such as person 690. Device 600 is configured to compare the sound and/or image data to sound and/or image data associated with a patient who is to receive the invasive procedure using the medical device, based on information from a database 624. Output data is generated based on the comparison. For example, in a check-in scenario, if the person 690 is recognized as a patient having a patient record in database 624, the output data may trigger an automatic patient check-in process by, for example, updating the patient's record in database 624 to indicate the patient has arrived for a medical procedure or is otherwise present. Alternatively, if patient 690 is wearing device 600, device 600 may be configured to identify patient 690 and transmit a signal indicative of the authentic identification of patient 690 to a computer, such as device 600 on person 694's head. The identification of patient 690 may include name, birth date, social security number, home address and/or other identification information stored in memory of the device on person 690's head and/or stored in another computer, such as procedure database 624. Device 600 may be able to identify patient 690 in any of a number of ways, such as by scanning a fingerprint of patient 690 at the time of check-in, scanning a retina of patient 690 at the time of check-in, assessing a unique movement pattern of patient 690, or otherwise sensing and/or authenticating the identity of patient 690.

In another embodiment, a device 600 on patient 690's head may be configured to check an identity of person 694, for example using facial or body recognition, voice recognition, etc. This may be useful in the case where person 690 wishes to confirm that person 694 is an employee of or otherwise acting under the authority of the medical facility when person 694 is asking for personal information of person 690. In this embodiment, device 600 on patient 690's head may be configured to communicate via a wireless network with a database, web page or other network destination to receive confirmation that the person 694 is authorized to receive personal information from person 690. For purposes of cybersecurity, device 600 and a database networked therewith may be configured to verify or ensure credentials of a medical professional programming a medical device and/or the program entered into the medical device. A processing circuit on device 600 may be configured to generate output data based on a comparison of input data (e.g., sound data, image data, etc.) to data in a database regarding known medical professionals. If the medical professional is known or otherwise authorized to use the medical device, the processing circuit may provide a suitable indication, for example, which may enable the medical device to be programmed, a procedure to be started, etc.

In a procedure scenario, the person 690 who checked in may be verified by another head-mounted device 692 to confirm the proper patient receives the proper procedure as stored in procedure database 624. A head-mounted display or database 624 may provide an authorization or enabling message to medical device 604 only upon confirmation by such computer that person 690 is the correct patient to receive the medical procedure. In another example, the output data may comprise a message to be displayed on a display. For example, the message on the patient 690's head-mounted display 698 may state, "Welcome, Mr. Jones. We are ready for your procedure for a blood donation." The message on a clinician's head-mounted display may say, "Mr. Jones is confirmed for a blood donation. Please direct him to room 101." Other messages and output data are contemplated. Patient 690 may be identified by clinician 693's head-mounted device 692 and/or by patient 690's head-mounted device 698 and the identification may occur by facial or body recognition, voice recognition, retinal scan, and/or other biometric input data.

In a case where person 690 is wearing a head-mounted display device, a forward facing camera may be used, for example, to acquire a retinal scan of person 690 and send the retinal scan data or authentication data to device 600 or database 624 to confirm the identity of person 690.

In one embodiment, device 600 may perform a check-in without requiring user input, i.e., automatically, upon detection of the person in the vicinity of device 600. The image data may comprise an image of a face of the person, sound of the person's voice, detection of an RFID tag associated with the person, an image of a wristband worn by the person, or other detection or identification methods. According to an embodiment, device 600 may automatically configure and/or program a device based on the location and/or detection of a patient. For example, when used with an apheresis device, device 600 may be configured to program or enable a configuration on the apheresis device with predetermined draw and return flow rates, anticoagulant (e.g., ACD) ratio, etc. by way of a network communication with the apheresis device. Configuration or programming may further comprise an indication of a product or products to be collected, e.g., single, double, triple platelet with concurrent products such as plasma (with specific volumes), red cells, etc. Configuration or programming may further comprise arm preference (left or right).

As another example, when used with an infusion pump, device 600 may be configured to program or enable a configuration on infusion device with predetermined return flow rate, drug dosing in milligrams (or milliliters) per minute. Configuration or programming may further comprise confirming the correct drug is being used (e.g., with reference to a prescription stored in a database in communication with device 600 and/or the infusion device). Configuration or programming may further comprise an indication of arm preference (left or right).

As another example, device 600 may be configured to work with other medical devices or other computing devices to determine the proper body proportions and body mass to pre-program or ensure the correct amount of anesthesia is set and being delivered. Device 600 may further be used to confirm the correct side of the patient is being operated on (e.g., remove the right kidney NOT the left).

In one embodiment, the procedure is compared to patient data stored in a database to determine compatibility. For example, a procedure to donate blood may not be compatible with a patient who has patient data indicating a low blood iron content. As another example, a procedure to donate plasma may not be compatible with a patient below a predetermined weight. In another example, a procedure to infuse a patient with a medicament may have limited compatibility with a patient, such as a maximum infusion rate based on a person's weight, height, or other characteristic.

Figure 7:
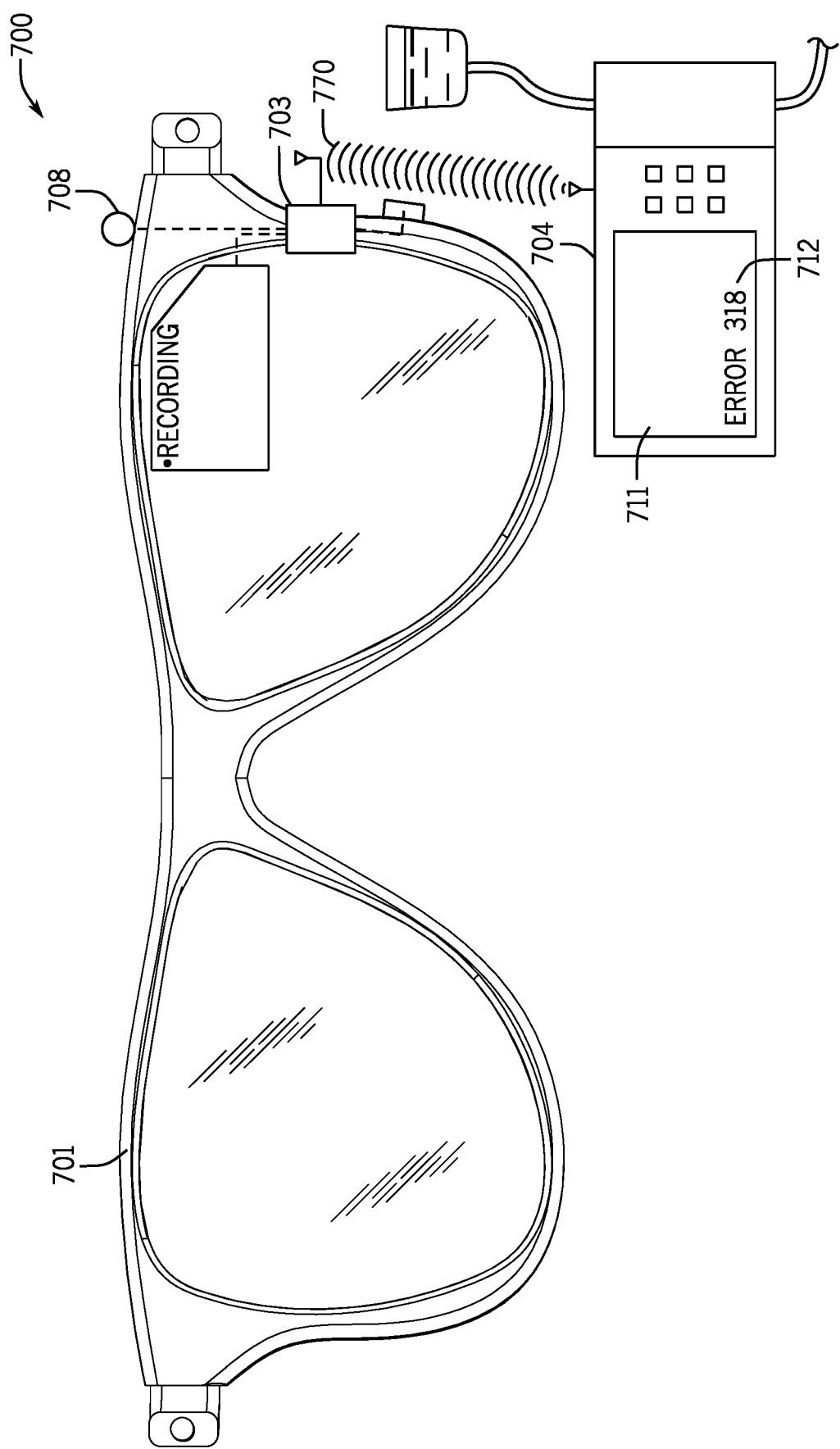
FIG. 7 is an illustration of a head-mounted display device for recording medical device information in response to a notification message, according to an illustrative embodiment.

Referring now to FIG. 7, a head-mounted display device for recording medical device information in response to a notification message will be described. In one example, device 700 may be configured to record and/or image error conditions of medical device 704 and/or report complaints, etc. A processing circuit 703 coupled to frame 701 of device 700 may be configured to receive a notification message from medical device 704, for example via communication link 770 (e.g., Wi-Fi, Bluetooth, Ethernet, etc.). The notification message may be merely an instruction to acquire medical device information (e.g., snap a picture, record a code, etc.), which may specify the type of information to acquire (e.g., video, image, image of specific component, etc.) and which may or may not be sent in response to an alert, error, caution, warning or alarm condition of device 704 or as a matter of course in a particular procedure.

Medical device 704 may be any medical device, such as one configured to perform an invasive procedure on a patient, such as an infusion, an apheresis procedure, a feeding pump operation (enteral or parenteral), etc. Processing circuit 703 may further be configured to record medical device information in response to receiving the notification message from the medical device.

The medical device information may be a video of the medical device acquired for a predetermined period of time (e.g., less than 5 seconds, less than 30 seconds, etc.) as seen by camera 708. The medical device information may comprise at least one error code received from the medical device via the wireless transceiver, via link 770 or another communication link. The error code may identify an error condition of device 704 (e.g., software error, fluid detected in air detector, hemoglobin detector out of range, no saline detected, high pressure in the line, low plasma detected, weigh scale disturbed, no blood flow, occlusion detected, reservoir overflow, etc.).

The medical device information may comprise an image of a display 711 of the medical device. In this example, in response to receiving the notification, device 700 is configured to determine an error code from the image of the display of the medical device (e.g., "error 318"), which may be determined by optical character recognition of an image of text on screen 711.

Processing circuit 703 may record the medical device information in response to receiving the notification message without requiring user input, for example, automatically. Alternatively, circuit 703 may begin to acquire the medical device information in response to a user input, such as a voice command "begin recording," pressing a button, shaking device 700, or other user input.

Figure 7A:
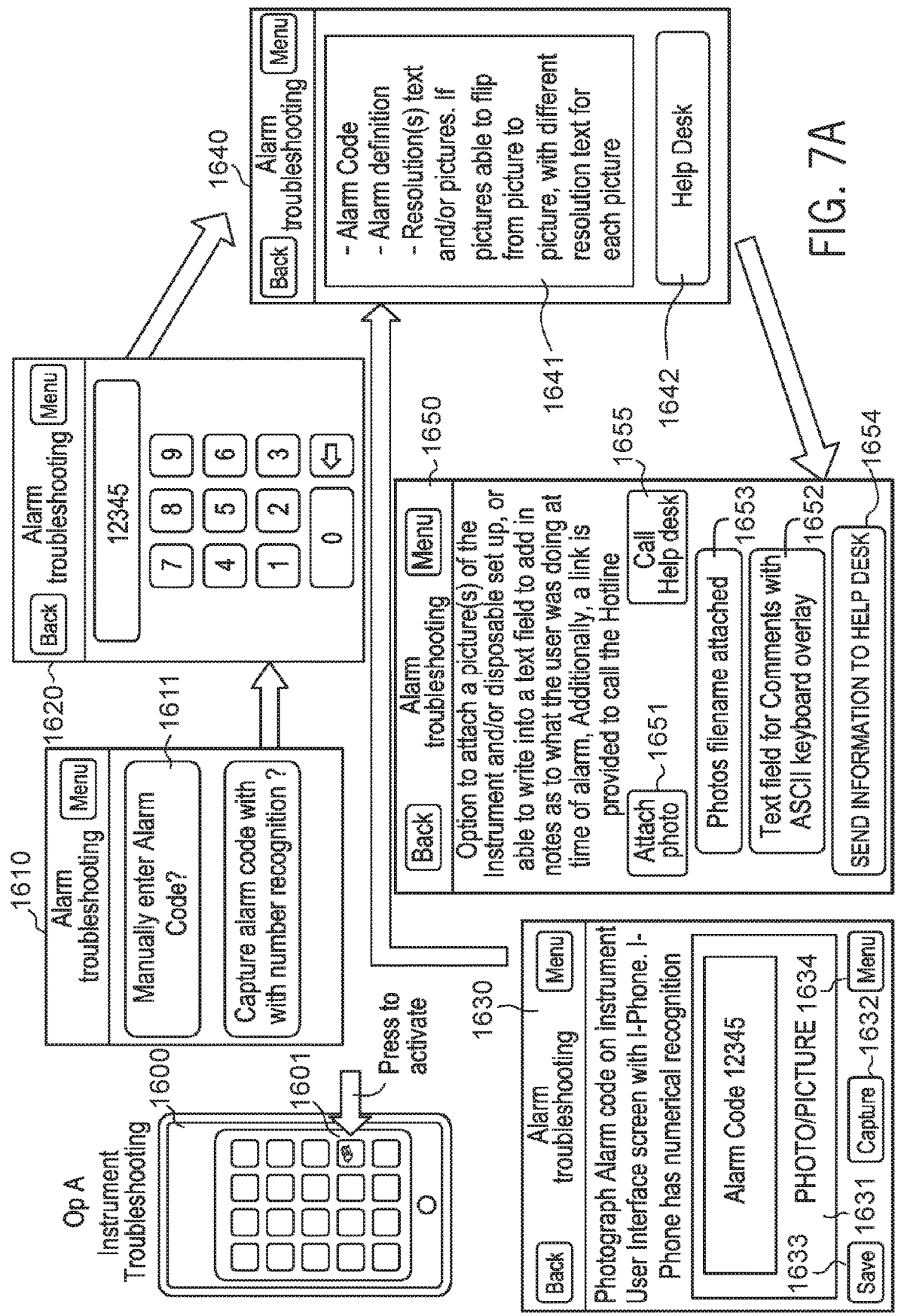
FIG. 7A shows example interfaces for blood collection device operators who are wearing a head mounted display device, according to an illustrative embodiment.

FIG. 7A shows example interfaces for blood collection device operators who are wearing a head mounted display device. For an operator, an example application operating on the display device can provide instrument troubleshooting. For example, the operator can enter an alarm code or take a picture of the alarm screen or kit configuration of a medical device. The application can present possible solutions; provide video(s) to resolve issue(s) if needed/desired/configured; use picture recognition and help access kit setup issues and provide resolutions; link to a hotline; etc.

In certain examples, the application can provide blood products available to be collected based on donor characteristics. The application can communicate how long the collection would take and the number of people helped based on the collection, for example. The application can allow for the transfer of procedure information and log files from an instrument using a communication protocol/medium such as Wi-Fi, Bluetooth, etc. In certain examples, the application can trigger/push instrument alarms or procedure information to an operator (e.g., receive a text message when an alarm occurs and provide links to troubleshooting if needed/desired/configured). The application can provide a real time scorecard (e.g., a goal was to collect 15 units with an average turnaround time of 55 minutes). The application can keep track of progress and report it back to an administrator, for example. An operator can also see a "scoreboard" on how the operators/teams are doing, e.g. team competitions. The application can enable the operator to photograph a label on a product bag and check to help ensure that the bag and donor are correct and that the correct blood type was labeled.

As shown, for example, in FIG. 7A, a computing device 1600, such as a smartphone or other computer, can provide an operator application 1601. The application 1601 can include an alarm troubleshooting interface 1610 to assist a device operator in troubleshooting an alarm or error triggered at a blood collection device, for example. The alarm troubleshooter 1610 can provide the operator with an option to enter an alarm code 1611, such as via a keypad 1620 of a mobile device in the vicinity of the head mounted display. The alarm troubleshooter 1610 can also provide the operator with an option to capture an alarm code with number recognition 1612, such as via a capture screen 1630. The capture screen 1630 shown in the example of FIG. 7A allows a user to capture, such as using a camera on head-mounted display, an alarm code shown on a collection device 1631. Via the capture interface 1630, the user can capture 1632, save 1633, and/or delete 1634 a captured image with code 1631.

Following input of an alarm code, either through manual entry or photo capture, an alarm troubleshooting guide 1640 is displayed. The troubleshooting guide 1640 provides information 1641 including an alarm definition for the alarm code along with materials to help the user resolve the alarm. For example, text and/or images to assist the operator in resolving the device alarm can be provided via the interface 1640. The operator can use the interface 1640 to flip between a series of pictures/images along with supporting resolution text for each picture to resolve the alarm, for example. A help desk option 1642 can be provided to assist the operator in resolving the alarm, for example.

Selecting the help desk option 1642 brings the operator to a help desk screen 1650. The help desk screen 1650 provides the user with an opportunity to attach a photograph 1651 of an instrument and/or disposable set up at issue. The user can also provide information via a text field 1652 regarding the problem. A listing of photos and/or files attached 1653 can be provided for user confirmation, and the user can submit 1654 the information to the help desk. Additionally, an option can be provided for the user to call the help desk 1655 According to another embodiment, device 700 may be configured to report a complaint. For example, device 700 may be configured to receive voice commands from a user to move through a menu structure stored in memory and presented to the user on the display of device 704. The menu structure may comprise data relating to categories of complaints, malfunctions, errors, troubleshooting tips, etc. For example, a first menu item may be "File a complaint." Upon selection by the user of the "File a complaint" data element, a "Complaint type" list may be presented to allow a user to select from a plurality of complaint types. For example, a user may choose "Leak," in response to which the device presents a list of components that may have a leak. A user may then select "ACD spike." Device 700 may then be configured to present a picture or image of the kit with the component highlighted to allow the user to confirm the component selected. Once confirmed, device 700 may be configured to transmit a report (e.g., indicating a failure, defect, etc.) to a manufacturer of the component or internally to a biomedical engineering department. In addition, any instruction on returning the kit could also be provided (e.g., providing mailing address, shipping information, contact information, etc.).

Figure 8:
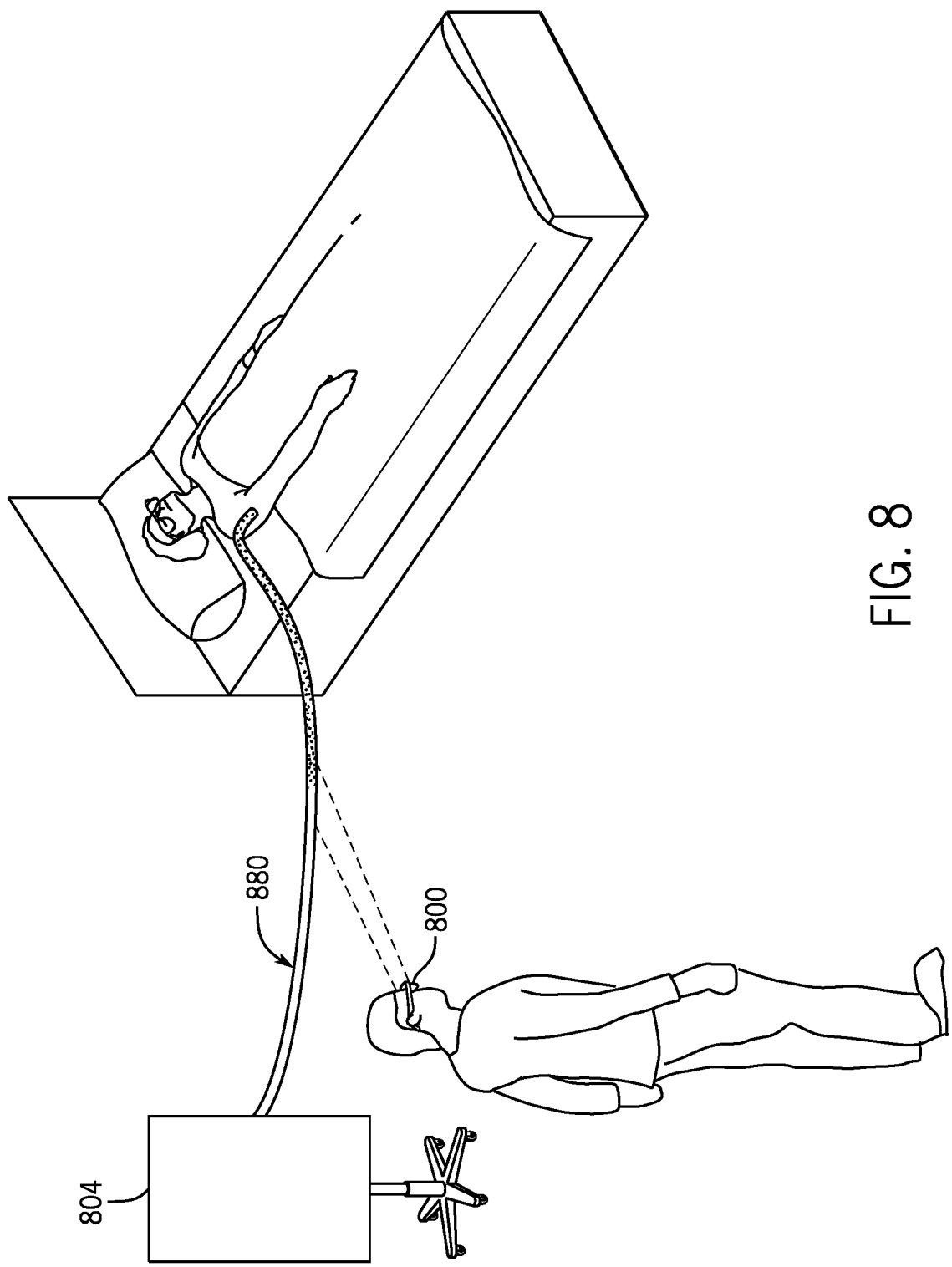
FIG. 8 is an illustration of a head-mounted display device for determining a characteristic of blood flowing through a component of medical device, according to an illustrative embodiment.

Referring now to FIG. 8, head-mounted display device for determining a characteristic of blood flowing through a component of a medical device will be described. Blood characteristics (e.g., donor hematocrit such as initial donor hematocrit just prior to the beginning of a medical procedure, lipemia, hemolysis, platelet clumping, blood clot, particulate in final product bag, bacterial contamination in final product (post storage), etc.) may be observed, identified and/or monitored using a camera and image processing algorithms or techniques. For example, donor hematocrit may be determined by visual observation based on blood characteristics such as color, hue, density, opaqueness, cloudiness, etc. upon the start of a blood donation, wherein blood begins flowing through tubing 880, or at various, regular, periodic or intermittent intervals during the procedure. Observation may further be made of a final separated product present in a bag.

Device 800, while worn by a clinician, may be configured to acquire an image of a component of the medical device, either automatically without requiring user input, or in response to user input. Device 800 may be configured to determine a characteristic of blood flowing through the component of the medical device and to generate output data based on the determination. The output data may be a visual and/or audible notification (e.g., message, alert, alarm, indication, etc.) that the blood characteristic has exceeded a threshold, a textual indication of a measure of the characteristic, a wireless message sent to a remote computing device such as the medical device 804 which may take some further action, such as pausing, stopping, or ceasing the medical procedure automatically (i.e., without requiring further user input), triggering an alarm on the medical device 804, sending a message over a wired or wireless network to a portable electronic device of a clinician, or other actions. This type of data can be tracked, stored in memory, and/or reported on a display over time in order to store trending data during a procedure or across multiple procedures.

Device 800 may be configured to operate a plurality of algorithms on one or more images of the component containing blood to detect any of a variety of characteristics (e.g., conditions) of the blood, such as hemolysis, lipemia, icterus, presence of particulate matter, discoloration, bacterial contamination, foreign objects, fibrin strands, etc.

In one example, a grossly lipemic WB/RBC will appear similar to a strawberry milkshake, while a lipemic plasma or platelet component may have an opaque or milky appearance.

Device 800 may be configured to make the determination by transmitting at least a portion of an image via a wireless transceiver to a remote computer and receiving data indicative of the characteristic of the blood flowing through the component. In this server-based embodiment, more advanced image processing algorithms may be run due to higher processing power typically available from a server farm or other server computer. A plurality of server computers sharing resources in a networked environment may be used to process the images. Alternatively, the determination may be made using processing resources on device 800.

The component may be a disposable or non-disposable component of medical device 804. For example, a cartridge, tubing and one or more blood bags may be a disposable component for collecting blood from a blood donor using medical device 804. Device 800 may be configured to image one or more portions of these elements of a disposable component. A disposable component may be a single-use component intended to be used on a single patient and/or for a single procedure and thereafter disposed of.

In another embodiment, device 800 may be configured to analyze images of blood seen by a clinician during a surgical procedure (e.g., on gauze used within the body or on a dedicated test strip). In this embodiment, device 800 may be configured to identify blood loss by looking at or acquiring an image of the color of the gauze or other test strip and comparing the acquired image to predetermined data regarding a characteristic represented by the color.

In another embodiment, device 800 may be configured to monitor donor or patient biologics (e.g., pulse or heart rate, eye dilation, temperature, facial flushing, fainting, etc.) during a procedure using a medical device as described herein, during surgery, etc. The monitored biologics can be reported directly on device 800 or can be compared to predetermined thresholds or other data to determine whether to provide a notification (e.g., message, alert, alarm, etc.) to a user of device 800 to bring to the user's attention a condition of the patient or donor.

In another embodiment, a disposable component may be imaged by taking photos of the kit and bags to determine the amount of fluid that remains in certain areas and based on the color of the fluid (and an input of donor Hct), it could be estimated the amount of red cells within certain areas of the kit.

In another embodiment, device 800 may be configured to assist a clinician in identifying a donor's veins for purposes of either patient identification (analogous to fingerprinting) or to assist the clinician in finding a vein for insertion of a needle of a medical device as described herein.

Figure 9:
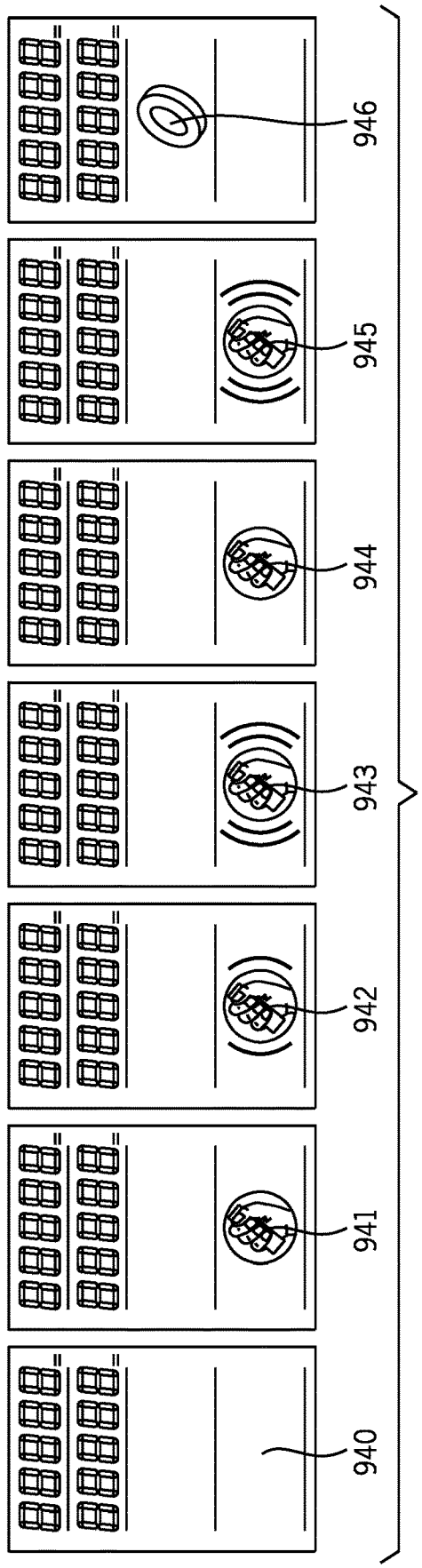
FIG. 9 is a series of screens displayed by a head-mounted display device for interface with a medical device configured to remove blood from a patient, according to an illustrative embodiment.

Referring now to FIG. 9, head-mounted display device for interface with a medical device configured to remove blood from a patient will be described. In this embodiment, a blood removal device (e.g., apheresis device, transfusion device, blood donation device, etc.) may be configured to communicate with a head-mounted display device worn by a patient/donor to indicate to the donor when to squeeze their hand and/or with how much intensity. The indication may be provided to the donor by way of an audible output from the head-mounted display device (e.g., a spoken command, alarm, etc.), displayed on a display, vibration, and/or other sensory outputs to the patient. In other embodiments, other indications may be given to a patient or clinician to do certain tasks or take certain actions at predetermined times or conditions during a medical procedure. In another embodiment, the head-mounted display device may be worn by a clinician and audio output may be provided with suitable volume to instruct the patient/donor and clinician.

FIG. 9 provides examples of indications on a display of a head-mounted display device that may be provided to a donor in the form of donor blood flow indicators 940-946. If no indicator (e.g., no first) is shown 940, then the donor can relax, for example. A first indicator 941 (e.g., a first) instructs the donor to lightly squeeze and/or squeeze with light frequency. A second indicator 942 (e.g., a first with one bar) instructs the donor to squeeze normally and/or with a normal frequency. A third indicator 943 (e.g., a first with two bars) instructs the donor to squeeze hard and/or with more frequency. In certain examples, a color of the indicator (e.g., blue or red) can change to indicate a state of blood flow, collection progress and/or degree of squeezing needed. For example, a blue first and/or bars 941-943 can change to a red first and/or bars in indicators 944-945. In certain examples, the indicator can flash to instruct the donor regarding the frequency of squeeze. A completion indicator 946 appears when the blood collection process has been completed.

A processing circuit of the head-mounted device may be configured to receive an instruction from the medical device, the instruction relating to removal of blood from the patient (e.g., squeeze intensity, procedure completed, volume collected, target volume, etc.). The processing circuit may be configured to provide an indication of the instruction to at least one of the display and another output circuit for the patient. Other output circuits may comprise a vibration device or other haptic feedback device, a sound transducer (e.g., a speaker or a sound transducer coupled to a headphone interface circuit), etc. For example, increase in haptic feedback (i.e. vibrations) could be made to indicate to the donor that more/harder squeezes are required. Further, haptic feedback could be made to a head-mounted device worn by an operator of the device to let them know that there is an issue with the donor/instrument.

The head-mounted display device may receive the instruction message (e.g., a bit, flag, data message, etc.) directly from the medical device via a local wireless network (e.g., a Bluetooth network, Wi-Fi, Zigbee, short-range wireless network, personal area network, etc.). Alternatively, the head-mounted display device may receive the instruction from a remote computer in communication with the network, the remote computer receiving the signal from the medical device over a second network (e.g., Ethernet).

In another embodiment, the head-mounted display device worn by the patient may be configured to receive voice commands from the donor/patient that can be interpreted and acted on. For example, the patient/donor may audibly state that help is needed or that they do not understand the instructions. The head-mounted display device may be configured to interpret the command and take an action, such as alerting a nearby clinician by way of a wireless message (e.g., text message, pager message, etc.) that assistance is needed and/or an indication (e.g., volume, number of vibrations, etc.) of the severity, urgency or importance of the request for assistance.

In another embodiment, the head-mounted display (or heads-up display or HUD) could also be used to assess eye pupil feedback (change in shape or eye movement), which could be indicative of the donor's/patient's change in emotional state, i.e. scared, confused, etc. A similar technique could be made on an operator (of, for example, apheresis or infusion pumps) to assess their confidence in the setting up or changing of a procedure parameter. Based on this assessment the instrument could provide additional confirmations or help options to minimize operator error. Additionally, if the parameters were set at a very high end, i.e. a potential dangerous dose to a patient, and the operator seems to be in an inappropriate state, the HUD could keep the change from being implemented or could inform a supervisor by way of an electronic message, alert, etc.

In another embodiment, the head-mounted display device worn by the patient may be configured to display entertainment such as videos, movies, games, etc. for the patient during the process. When instructions are needed, such as to indicate desired squeeze frequency and/or intensity or to indicate the procedure is complete, the instruction messages may be displayed as an overlay over part of the entertainment being displayed. Entertainment may be streamed from a remote source, or played from a local memory on head-mounted display device. In one example, a calming scene may be played along with calming music to reduce patient/donor anxiety during the medical procedure. In one embodiment, head-mounted display may comprise a virtual reality engine configured to provide video, audio and/or other sensory stimuli to give the wearer a simulated physical presence in places in the real world or imagined worlds.

In one embodiment, the information and/or instruction is derived from collected sensor data regarding donor vein and blood pressure feedback, collected volume at the system, weight scale readings of a collection bag, pressure sensors within the apheresis device, etc.

In another embodiment, the indication to the patient/donor may comprise a target collection volume for the donor, which may be a value programmed into the blood collection system by the operator for the donor. The volume collected so far and target collection volume for the donor may be both displayed in the same numerical units.

Figure 10:
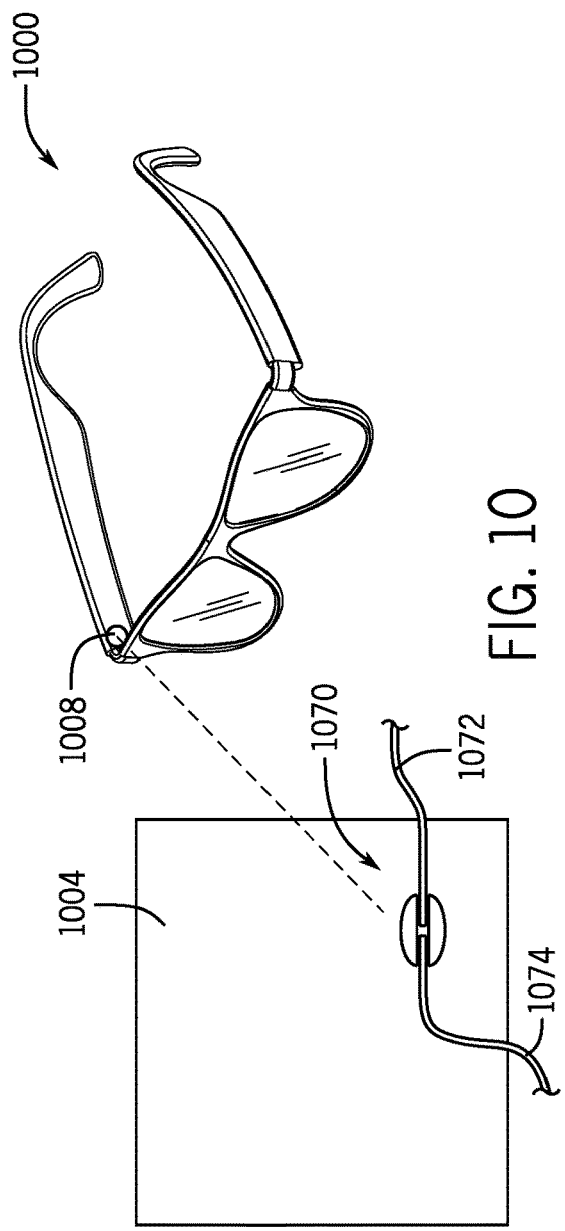
FIG. 10 is an illustration of a head-mounted display device for authorizing a feature based on visual cues, according to an illustrative embodiment.

Referring now to FIG. 10, a head-mounted display device for authorizing a feature based on visual cues will be described, according to an illustrative embodiment. For example, if the head-mounted display device sees genuine inventory or a certain number of inventory/kits, the device will authorize the medical device 1004 to perform a step.

One feature that may be improved with an authorization feature is sterile docking. Sterile docking may refer to a process in which two tubes are joined together in a sterile manner using heat. Apheresis machine 1004 comprises an integrated dock station 1070 on the machine configured to join together two tubes using heat. If an operator of machine 1004 lines up a docking kit 1072 to a kit 1074 already loaded on the device 1004 in the docking station 1070, device 1000 may detect this event using camera 1008 and an image processing algorithm that continually compares what is seen or imaged by camera 1008 to predetermined known patterns stored in memory. A processing circuit of device 1000 is configured to acquire an image of docking station 1070 of medical device 1000 with camera 1008, to process the image to identify the presence of two tubes lined up for a sterile docking (e.g., in the vicinity of each other and/or docking station 1070) and to determine whether docking station 1070 and/or the kits 1072, 1074 are authorized for this use. For example, a manufacturer of device 1004 may have a limit on the number of times docking station 1070 may be used, for example in a period of time or depending on the number of kits purchased. Device 1000 may be configured to enable docking station 1070 (by a wireless message to a processing circuit within medical device 1004) if there are remaining "docks" left (as determined by reference to a number of docks left stored in device 1004, device 1000 or in a remote computer. In one example, the number of docks remaining is stored in a database on device 1004 or in another computer in communication with device 1004, and a plurality of head-mounted devices 1000 may each report to the database whenever a docking is detected.

This embodiment may be applied to other components or features of device 1004 and device 1000 may detect other characteristics of device 1004 or components thereof to make the determination as to whether their use is authorized. For example, device 1000 may acquire an image of a disposable component held in front of device 1004 to determine whether the component is compatible with device 1000. The disposable component may be identified using any of a number of technologies, such as a QR code, an RFID tag, image recognition of a portion of the disposable component, etc. Device 1000 may then send the identification of the disposable component to a remote database or local memory of components to determine whether the component is authorized. A secure message may then be transmitted by device 1000 to device 1004 to authorize or not authorize a procedure to be carried out using device 1004.

In one embodiment, a medical device 1004 may be authorized to only operate with a disposable component that meets certain compatibility criteria. In this case, head-mounted device 1000 may be configured to detect with its camera whether the disposable component meets the compatibility criteria, for example by looking for a particular feature or aspect of the kit, by looking for or otherwise detecting an identifier code associated with the kit, etc. In another embodiment, medical device 1004 may only be authorized to operate with a predetermined number of disposable components. In this case, one or more head-mounted devices 1000 may be configured to count a number of times medical device 1004 is used with a different disposable component and store this information in a database local to device 1000 or remote thereto. When a limit has been reached, a computer in communication with the database may send a message to medical device 1004 and/or head-mounted device 1000 (which may then forward the message to medical device 1004) indicating the limit has been reached, disabling further use of medical device 1004, providing information about how more uses may be obtained, etc.

In various embodiments, head-mounted device 1000 may be configured to continually monitor images from its camera to detect a known condition, based on comparison to pre-stored image characteristics. Alternatively, monitoring may be initiated or activated by user input. In another embodiment, monitoring may be activated by a determination by device 1000 or device 1004 that the devices are in proximity of each other, for example using near-field communication, a Bluetooth communication, an infrared signal, a motion detector, or other sensors on device 1000 and/or device 1004.

In another embodiment, a head-mounted device could be used to authorize a user to use a medical device or instrument. For example, a camera on the head-mounted device may be configured to acquire a biometric indicator of a person wearing the camera, such as an image of a person's hand or finger, a retinal scan from a user-facing camera, a sample of a person's voice authenticated by a voice recognition algorithm operating on the head-mounted device, etc. The head-mounted device and/or medical device may be configured to determine whether the user is authorized to use the medical device and, optionally, may also be configured to determine what features or functions of the medical device the person is authorized to use, selected from a group of features or functions.

In another embodiment, after a user has used the medical device, the medical device may be configured to determine that communication with the head-mounted device has been lost, or the head-mounted device is otherwise no longer present or in the vicinity of the medical device (for example, using a near-field communication device, personal area network, or other technology). In any of these cases, the medical device may be configured to lock down the instrument (e.g., using an NFC handshake), for example by preventing access to one or more or all of the features or functions of the medical device. For example, the medical device may be configured to lock a setting of the device so that the setting cannot be changed after the user has left the vicinity of the device by other users. Optionally, the medical device may be configured to lock a setting of the device so that the setting cannot be changed after the user has left the vicinity of the device by other users unless the other user is on a list of authorized users stored in memory. The list of authorized users may comprise multiple levels of access for different types of users, such as User Type A may access and change all features or settings, User Type B may access or change only settings X and Y, and User Type C may not access or change any settings. For example, on an infusion pump only certain authorized users could change a flow rate setting.

In another embodiment, the medical device may be configured to use a NFC or other communication device in communication with the head-mounted display to record in a database information about a user's interaction with the medical device. For example, the medical device could be used to track the user, and when and what settings were changed on the medical device when that user was present. A list of users and their respective setting changes may be kept in the medical device for later retrieval and analysis for such tasks as training, improvement in care delivery, evaluation, and error analysis.

ADDITIONAL EMBODIMENTS

According to another embodiment, a head-mounted display such as that described herein may be used for data input to apheresis and blood component processing devices, enteral/parenteral pumps, and infusion devices. The data input may be human eye-controlled data input and/or programming of medical devices or data input to databases.

According to another embodiment, a head-mounted display such as that described herein may be used for motion controlled data input and/or programming (to devices, from devices, to database, from database, etc.).

According to another embodiment, a head-mounted display may be used for visual and/or haptic feedback for data transfer and procedures from other devices to a person wearing the head-mounted display.

According to another embodiment, real time instrument status, notifications, and/or alarms may be displayed and/or haptic feedback may be provided to a head-mounted display based upon actual user location (e.g., if a user is in a room or within a predetermined distance of the medical device) and/or on demand (e.g., in response to a request from the user for such information).

According to another embodiment, a head-mounted display device such as that described herein may be configured to perform scheduling (e.g., appointments, blood donations, medical procedures, etc.), which may be displayed in real time and/or upon operator request. For example, an intake clinician may speak information received from a patient into a microphone of a head-mounted display device to populate a patient record, search for an schedule an appointment, check-in the patient for the appointment, schedule a follow-up appointment, etc.

According to another embodiment, a barcode reader may be implemented by a processing circuit of a head-mounted display device for kit and/or blood product tracking, identification, and data entry into machines and devices.

According to another embodiment, a photo application may be implemented on a head-mounted display device for onscreen product identification, device ID, inventory control, tracking, etc.

According to another embodiment, real time updates may be provided to donor, device, center, medical records, etc. enabled with voice and/or photo updates to or from a head-mounted display device.

The devices described herein can make any of the determinations, comparisons, calculations, analyses, etc. described locally and/or by sending a request to a server to do the processing.

A head-mounted display device for use in a medical facility may comprise a frame configured to be mounted on a person's head, wherein the person has a view of the medical facility relative to the frame; a display; a wireless transceiver configured to communicate with a network; and a processing circuit coupled to the frame, the display and the wireless transceiver, wherein the processing circuit is configured to receive information regarding a location of a medical product or patient via the wireless transceiver, to provide a visual indication of the location on the display, to detect a change in the view of the person and to change the visual indication of the location on the display in response to the detected change in view. The medical facility may be a blood donation facility, wherein the medical product comprises a blood donation kit. The patient may be a blood donor. The visual indication of the location may comprise a graphical representation in the person's view of the medical facility through the frame. The display may comprise a display surface configured to reflect projected images representing the visual location and to allow the person to see through the display surface. The visual indication may comprise a graphical or textual description of the location comprising at least one of a distance and a physical description. The location may be received from a remote database comprising location data for a plurality of different medical products or different patients. The processing circuit may be configured to detect the change in view of the person based on at least one of an accelerometer and a gyroscope. The processing circuit may be configured to detect the change in view of the person based on a calculated physical location of the device. The location may be generated by the processing circuit based on signals received from the wireless transceiver. The location may be generated using a near field communication technology. The location may be a location relative to the device. The processing circuit may be configured to receive an inventory data representing a number of the medical product in inventory, the processing circuit configured to display the inventory data on the display. The displayed inventory data may be displayed in the person's view of the medical facility through the frame in a screen location related to a location of the medical product in the person's view. The processing circuit may be further configured to receive at least one of information regarding a quantity, manufacturer and expiration data for the medical product. The medical product may be for use in an infusion or feeding operation.

A system for use in a medical facility may comprise a blood treatment machine operable with a disposable medical product; a frame configured to be mounted on a person's head, wherein the person has a view of the medical facility relative to the frame; a display; a wireless transceiver configured to communicate with a network; and a processing circuit coupled to the frame, the display and the wireless transceiver, wherein the processing circuit is configured to receive information regarding a location of the disposable medical product via the wireless transceiver, to provide a visual indication of the location on the display, to detect a change in the view of the person and to change the visual indication of the location on the display in response to the detected change in view. The blood treatment machine may comprise an apheresis machine.

A head-mounted display device for use in a medical facility may comprise a frame configured to be mounted on a person's head, wherein the person has a view of the medical facility relative to the frame; a display; a wireless transceiver configured to communicate with a network; and a processing circuit coupled to the frame, the display and the wireless transceiver, wherein the processing circuit is configured to receive information regarding a location of a medical product or patient via the wireless transceiver, to provide a visual indication of the location on the display, wherein the visual indication comprises an identifier of the medical product or patient and a physical description of the location of the medical product or patient, to detect a change in the view of the person and to change the visual indication of the location on the display in response to the detected change in view. The physical description may be at least one of a room number and a compartment identifier.

A head-mounted display device for interface with a medical device configured to perform an invasive procedure on a patient may comprise: a frame configured to be mounted on a person's head; a display; a camera; a wireless transceiver configured to communicate with a network; and a processing circuit coupled to the frame, the display, the camera and the wireless transceiver, wherein the processing circuit is configured to acquire an image of a component of the medical device with the camera, to process the image to identify a characteristic of the component, to compare the characteristic to predetermined data for the component, and to generate output data based on the comparison. The component may be a display of the medical device. The image may be processed to determine data programmed into the medical device by the person, wherein the identified characteristic is a programmed value. The predetermined data may be a medical prescription and the output data is an indication as to whether the programmed data meets the medical prescription. The device may be configured to provide at least one of an audible alert and a visual alert in a case where the programmed data does not meet the medical prescription. In a case where the programmed data does not meet the medical prescription, the device may be configured to display an instruction to the person for correcting the programmed data. The medical device may be an apheresis device or an infusion device or a patient feeding device. The processing circuit may be configured to generate the predetermined data for the component based on an image acquired by the camera. The component may be a disposable component configured to be loaded into the medical device, wherein the characteristic of the disposable component is an indication of how the component is loaded into the medical device and wherein the predetermined data is data representing a proper loading of the component. The component may be a disposable component configured to be loaded into the medical device, wherein the predetermined data is data indicating a type of disposable component, wherein the comparison indicates whether the disposable component is of a known type. The predetermined data may represent a type of disposable component approved for use with the medical device. The output data may comprise a message indicating the disposable component is not approved for use with the medical device. The processing circuit may be configured to send a message wirelessly to a remote computer indicating the disposable component is not approved for use with the medical device. The medical device may be a transfusion apparatus, wherein the component is a blood transfusion bag. The characteristic may be a code printed on the blood transfusion bag, wherein the predetermined data is data associating the code with a particular patient. The characteristic may be a date indicative of expiration of blood within the blood transfusion bag. The processing circuit may be configured to acquire the image in response to a message received from the medical device. The message may be received by direct wireless communication between the head-mounted display device and the medical device or by communication between a remote server computer and the head-mounted display device. The processing circuit may be configured to receive at least two messages configured to trigger the acquisition of the image at different times during preparation or operation of the medical device. The device may be configured to detect a proper loading of a disposable component and to confirm the loading of an anticoagulant. The device may be configured to detect a proper programming of the medical device according to a medical prescription and to confirm a drug source is loaded into the medical device. The processing circuit may be configured to acquire the image in response to user input from the person wearing the head-mounted display. The user input may be received from a microphone or button.

A system may comprise a medical device configured to perform an invasive procedure on a patient; a frame configured to be mounted on a person's head; a display; a camera; a wireless transceiver configured to communicate with a network; and a processing circuit coupled to the frame, the display, the camera and the wireless transceiver, wherein the processing circuit is configured to acquire an image of a component of the medical device with the camera, to process the image to identify a characteristic of the component, to compare the characteristic to predetermined data for the component, and to generate output data based on the comparison. The medical device may be an apheresis device or an infusion device or a patient feeding device.

A head-mounted display device for interface with a medical device configured to perform an invasive procedure on a patient may comprise a frame configured to be mounted on a person's head; a display; a sensor; a wireless transceiver configured to communicate with a network; and a processing circuit coupled to the frame, the display, the sensor and the wireless transceiver, wherein the processing circuit is configured to receive at least one of sound and image data from the sensor, wherein the at least one of sound and image data is associated with a person in the vicinity of the device, to compare the at least one of sound and image data to the at least one of sound and image data associated with the patient who is to receive the invasive procedure using the medical device, and to generate output data based on the comparison. The sound data may comprise a sample of a voice of the person in the vicinity of the device. The processing circuit may be configured to use voice recognition to do the comparison. The image data may comprise an image of the person in the vicinity of the device. The processing circuit may be configured to use facial recognition to do the comparison. The device may be configured to acquire the image of the person in the vicinity of the device while the person in the vicinity of the device is wearing the device. The processing circuit may be configured to use a retinal scan to do the comparison. Both sound and image data associated with the person in the vicinity of the device may be compared to sound and image data associated with the patient who is to receive the invasive procedure using the medical device. The output data may comprise a message to be displayed on the display. The output data may comprise a command to the medical device to allow the procedure. The medical device may be a blood donation apparatus and the output data comprises a check-in message to check the patient in for a blood donation procedure. The processing circuit may perform the check-in without requiring user input. The image data may comprise an image of a wristband worn by the person in the vicinity of the device. The image data may comprise an image of a bar code associated with the person in the vicinity of the device. The sensor may comprise an RFID sensor configured to identify an RFID tag or transmitter worn by the person in the vicinity of the device. The procedure may be compared to patient data stored in a database to determine compatibility.

A head-mounted display device for interface with a medical device configured to perform an invasive procedure on a patient may comprise a frame configured to be mounted on a person's head; a display; a sensor; a wireless transceiver configured to communicate with a network; and a processing circuit coupled to the frame, the display, the sensor and the wireless transceiver, wherein the processing circuit is configured to receive at least one of sound and image data from the sensor, wherein the at least one of sound and image data is associated with a person in the vicinity of the device, to compare the at least one of sound and image data to the at least one of sound and image data associated with the patient who is to receive the invasive procedure using the medical device, and to generate output data based on the comparison, wherein the output data comprises a programming message configured to program an operational characteristic of the medical device configured to perform an invasive procedure on a patient. The programming message may be configured to program a blood product donation operation on the medical device.

A head-mounted display device for interface with a medical device configured to perform an invasive procedure on a patient may comprise a frame configured to be mounted on a person's head; a display; a sensor; a wireless transceiver configured to communicate with a network; and a processing circuit coupled to the frame, the display, the sensor and the wireless transceiver, wherein the processing circuit is configured to receive at least one of sound and image data associated with a person in the vicinity of the device, to compare the at least one of sound and image data to at least one of sound and image data associated with a medical professional who is to use the medical device and to generate output data based on the comparison, wherein the output data comprises an indication that the medical professional is approved to use the medical device.

A head-mounted display device for interface with a medical device configured to perform an invasive procedure on a patient may comprise a frame configured to be mounted on a person's head; a display; a wireless transceiver configured to communicate with a network; and a processing circuit coupled to the frame, the display and the wireless transceiver, wherein the processing circuit is configured to receive a notification message from the medical device, the medical device being configured to perform an invasive procedure on a patient, the processing circuit further configured to record medical device information in response to receiving the notification message from the medical device. The device may comprise a camera, wherein the medical device information is video of the medical device as seen by the camera. The medical device information may comprise at least one error code received from the medical device via the wireless transceiver. The device may comprise a camera, wherein the medical device information is an image of a display of the medical device. The device may be configured to determine an error code from the image of the display of the medical device. The processing circuit may record the medical device information in response to receiving the notification message without requiring user input. The medical device may be an infusion pump and the notification message is received in response to an occlusion in a line detected by the infusion pump. The medical device may be an apheresis machine. The medical device may be a feeding pump.

A head-mounted display device for interface with a medical device configured to perform an invasive procedure on a patient may comprise a frame configured to be mounted on a person's head; a display; a wireless transceiver configured to communicate with a network; and a processing circuit coupled to the frame, the display and the wireless transceiver, wherein the processing circuit is configured to receive an input signal, the processing circuit further configured to record medical device information in response to receiving the input signal, the processing circuit configured to display a response message on the display based on the recorded medical device information. The response message may comprise a confirmation message that the recorded medical device information has been recorded or received by a remote computer. The input signal may be received from a user input device. The processing circuit may be configured to automatically record the medical device information in response to receiving the input signal. The processing circuit may be configured to await a user input before recording the medical device information after receiving the input signal. The input signal may be received from the medical device. The input signal may comprise data regarding an error condition of the medical device. The medical device information may comprise an image of a disposable unit installed on the medical device.

A system for performing an invasive procedure on a patient may comprise a medical device configured to perform an invasive procedure on a patient; a head-mounted display device for interface with the medical device. The head-mounted display device may comprise a frame configured to be mounted on a person's head; a display; a wireless transceiver configured to communicate with a network; and a processing circuit coupled to the frame, the display and the wireless transceiver, wherein the processing circuit is configured to receive a notification message from the medical device, the medical device being configured to perform an invasive procedure on a patient, the processing circuit further configured to record medical device information in response to receiving the notification message from the medical device. The medical device may comprise an infusion pump, an enteral feeding pump or a blood processing device. The processing circuit may further be configured to receive a comment from a person about the operation of the medical device and to transmit the comment to a remote computer via the wireless transceiver.

A head-mounted display device for interface with a medical device configured to perform an invasive procedure on a patient may comprise a frame configured to be mounted on a person's head; a display; a camera; a wireless transceiver configured to communicate with a network; and a processing circuit coupled to the frame, the display, the camera and the wireless transceiver, wherein the processing circuit is configured to acquire an image of a component of the medical device, the medical device being configured to perform an invasive procedure on a patient, the processing circuit further configured to determine a characteristic of blood flowing through the component of the medical device and to generate output data based on the determination. The processing circuit may be configured to make the determination by transmitting at least a portion of the image via the wireless transceiver to a remote computer and receiving data indicative of the characteristic of the blood flowing through the component. The characteristic may be a hematocrit level of the blood. The component may be tubing. The component may be configured for use on a single patient. The processing circuit may be further configured to acquire additional images of the component at different times, to determine the characteristic of blood flowing through the component at the different times, and to store the determined characteristics in a memory device. The additional images may be acquired without requiring user input. The medical device may be an apheresis machine. The component may be a disposable component.

A head-mounted display device for interface with a medical device configured to perform an invasive procedure on a patient may comprise a frame configured to be mounted on a person's head; a display; a camera; a wireless transceiver configured to communicate with a network; and a processing circuit coupled to the frame, the display, the camera and the wireless transceiver, wherein the processing circuit is configured to image a disposable component of the medical device, the medical device being configured to perform an invasive procedure on a patient, the processing circuit further configured to determine a characteristic of blood in the disposable component of the medical device, to compare the characteristic to a predetermined threshold, and to generate a notification based on the comparison. The characteristic may be a blood hematocrit. The medical device may be an apheresis device. The disposable component may comprise a tube and a bag. The notification may comprise a signal to the medical device that a donation procedure may begin. The processing circuit may be configured to control the camera to acquire a plurality of images over time, determine a blood hematocrit for each image, and store the plurality of blood hematocrits in a file in a memory device.

A system for performing an apheresis procedure on a patient may comprise an apheresis medical device; a head-mounted display device comprising a frame configured to be mounted on a person's head, a display, a camera, a wireless transceiver configured to communicate with a communication network, and a processing circuit coupled to the frame, the display, the camera and the wireless transceiver, wherein the processing circuit is configured to acquire an image of a component of the apheresis medical device, the processing circuit further configured to determine a characteristic of blood flowing through the component of the medical device and to generate output data based on the determination. The processing circuit may be configured to transmit a signal based on the output data to the apheresis medical device. The apheresis medical device may be configured to stop an apheresis procedure based on the signal received from the processing circuit of the head-mounted display device. The processing circuit may be configured to make the determination by transmitting at least a portion of the image via the wireless transceiver to a remote computer and receiving data indicative of the characteristic of the blood flowing through the component. The component may be tubing.

A head-mounted display device for interface with a medical device configured to remove blood from a patient may comprise a frame configured to be mounted on the patient's head; a display; a wireless transceiver configured to communicate with a network; and a processing circuit coupled to the frame, the display and the wireless transceiver, wherein the processing circuit is configured to receive an instruction from the medical device, the instruction relating to removal of blood from the patient, the processing circuit further configured to provide an indication of the instruction to at least one of the display and another output circuit for the patient. The processing circuit may receive the instruction directly from the medical device via a local wireless network. The processing circuit may receive the instruction from a remote computer in communication with the network, the remote computer receiving the signal from the medical device over a second network. The indication may instruct the patient to squeeze a hand. The indication may comprise an icon of a fist. The indication may comprise text. The indication may further indicate an intensity with which the patient is to squeeze the hand. The another output circuit may comprise a vibration device. The another output circuit may comprise a sound transducer. The sound transducer may be coupled to a headphone interface circuit.

A head-mounted display device for interface with a medical device configured to remove blood from a patient may comprise a frame configured to be mounted on the patient's head; a display; a wireless transceiver configured to communicate with a network; and a processing circuit coupled to the frame, the display and the wireless transceiver, wherein the processing circuit is configured to receive an instruction from the medical device, the processing circuit further configured to provide an indication of the instruction the display, wherein the indication indicates an intensity with which the patient is to squeeze a hand. The indication may comprise an icon of a fist. The display device may further comprise a vibration device configured to vibrate in response to the instruction from the medical device.

A system for removing plasma from a donor may comprise a plasmapheresis device configured to separate plasma from red blood cells and return the red blood cells to the donor; and a head-mounted display device for interface with the plasmapheresis device. The head-mounted display device may comprise a frame configured to be mounted on the donor's head; a display; a wireless transceiver configured to communicate with the plasmapheresis device; and a processing circuit coupled to the frame, the display and the wireless transceiver, wherein the processing circuit is configured to receive a message from the plasmapheresis device, the message relating to a plasmapheresis procedure being performed on the donor, the processing circuit further configured to provide an indication of the instruction to the display for the donor to see. The indication may instruct the patient to squeeze a hand. The indication may comprise an icon of a fist. The indication may comprise text. The indication may further indicate an intensity with which the patient is to squeeze the hand. The plasmapheresis device may be configured to derive the instruction from a sensor on the plasmapheresis device. The plasmapheresis device may be configured to detect a low flow condition based on signals from the sensor and to generate the message to the head-mounted display device in response to the low flow condition.

A head-mounted display device for interface with a medical device configured to perform an invasive procedure on a patient may comprise a frame configured to be mounted on a person's head; a display; a camera; a wireless transceiver configured to communicate with a network; and a processing circuit coupled to the frame, the display, the camera and the wireless transceiver, wherein the processing circuit is configured to acquire an image of a component of the medical device with the camera, to process the image to identify a characteristic of the component, to determine whether the component is authorized for use, and to transmit a message to the medical device based on whether the component is authorized for use. The medical device may be an apheresis machine and the component may be a dock station. The characteristic of the component may be whether a disposable component is in the vicinity of the component. The characteristic of the component may be whether a disposable component is aligned with another disposable component installed on the device. The message may cause the device to enable the component for use. The determination may be made by checking a database for a number of uses of the component for the particular medical device.

A head-mounted display device for interface with a medical device configured to perform an invasive procedure on a patient may comprise a frame configured to be mounted on a person's head; a display; a camera; a wireless transceiver; and a processing circuit coupled to the frame, the display, the camera and the wireless transceiver, wherein the processing circuit is configured to acquire an image of the medical device with the camera, to process the image to identify a characteristic of the medical device, to determine whether the medical device is authorized for use, and to transmit a message based on whether the medical device is authorized for use. The medical device may be an apheresis machine. The characteristic of the medical device may be a number of times the medical device has been used in a predetermined manner. The message may cause the device to enable a single-use disposable component for use. The determination may be made by checking a database for a number of uses of the component for the particular medical device.

A system for performing an invasive procedure on a person may comprise a medical device configured to perform an invasive procedure on a person and a head-mounted display device for interface with the medical device. The head-mounted display device may comprise a frame configured to be mounted on a person's head; a display; a camera; a wireless transceiver; and a processing circuit coupled to the frame, the display, the camera and the wireless transceiver, wherein the processing circuit is configured to acquire an image of a component of the medical device with the camera, to process the image to identify a characteristic of the component, to determine whether the component is authorized for use, and to transmit a message to the medical device based on whether the component is authorized for use. The medical device may be an apheresis machine and the component is a dock station integral with the medical device. The characteristic of the component may be whether a disposable component is in the vicinity of the component. The characteristic of the component may be whether a disposable component is aligned with another disposable component installed on the device. The message may cause the device to enable the component for use. The determination may be made by checking a database for a number of uses of the component for the particular medical device. The component may be a disposable, single-use component. The component may comprise a tube configured to pass blood products therethrough. Authorization may be determined by reference to data in a database.

We claim:

1. A head-mounted display device for interface with a blood collection device configured to perform a blood collection procedure on a patient, comprising:
   a frame configured to be mounted on a person's head;
   a display;
   a wireless transceiver configured to communicate with a network; and
   a processing circuit coupled to the frame, the display and the wireless transceiver, wherein the processing circuit is configured to receive input data relating to an alarm or error triggered at the blood collection device for a problem encountered with using the blood collection device, the processing circuit further configured to retrieve from a memory step-by-step instructions for troubleshooting the problem encountered with using the blood collection device based on the input data, and to display the instructions relating to the blood collection device on the display.

2. The device of claim 1, further comprising a sound transducer, wherein the processing circuit is configured to control the sound transducer to output a sound relating to the instructions.

3. The device of claim 1, wherein the instructions comprise at least three step-by-step instructions, wherein the processing circuit is configured to display each of the at least three step-by-step instructions in a sequence, one after the other, wherein the instructions instruct a user how to respond to the alarm or error triggered at the blood collection device.

4. The device of claim 1, wherein the input data comprises notification data from the blood collection device indicating an error condition of the medical device.

5. The device of claim 4, the error condition is an occlusion in a line.

6. The device of claim 1, further comprising a camera coupled to the processing circuit, wherein the camera is configured to acquire an image of the blood collection device in response to user input at a user input device or without requiring user input at the user input device.

7. The device of claim 6, wherein the processing circuit is configured to detect a condition of the blood collection device from the acquired image and to generate the input data used to retrieve the instruction relating to the blood collection device.

8. The device of claim 1, wherein the instructions are retrieved and displayed automatically, without requiring user input.

9. The device of claim 1, wherein the instructions are training instructions configured to train the person how to use the blood collection device.

10. The device of claim 9, wherein the training instructions are presented on the display and are further related to a screen being displayed on the blood collection device approximately simultaneously.

11. The device of claim 9, wherein the instructions comprise a video or a GIF file, wherein the instruction video is configured to train a patient about a procedure to be implemented using the blood collection device.

12. The device of claim 11, wherein the instructions comprise a video, wherein the instruction video is configured to train a patient about a procedure to be implemented using the blood collection device.

13. The device of claim 1, further comprising a sensor configured to sense a motion or eye position of the person and to generate control signals for controlling the blood collection device based on the sensed motion or eye position.

14. A head-mounted display device for interface with a medical device configured to perform an invasive procedure on a patient, comprising:
- a housing configured to be mounted on a person's head;
- a display;
- a wireless transceiver configured to communicate with a network; and
- a processing circuit coupled to the housing, the display and the wireless transceiver, wherein the processing circuit is configured to receive a message indicating an error condition of the medical device, the processing circuit further configured to retrieve from a memory an instruction for addressing the error condition of the medical device based on the error condition of the medical device, and to display the instruction relating to the medical device on the display.

15. The device of claim 14, wherein the error condition is an occlusion condition indicating the presence of an occlusion in a tube of the medical device, wherein the instruction comprises an instruction for addressing the occlusion condition of the medical device, wherein the instruction comprises step-by-step instructions for addressing the occlusion condition of the medical device.

16. A head-mounted display device for use by a clinician with a blood collection device configured to perform a blood collection procedure on a donor, comprising:
- a frame configured to be mounted on a clinician's head;
- a display disposed in a field of vision of the clinician wearing the frame;
- a wireless transceiver configured to communicate with a network;
- a camera coupled to the frame and configured to acquire an image of the donor using the blood collection device; and
- a processing circuit coupled to the frame, the display, the camera and the wireless transceiver, wherein the processing circuit is configured to receive an image of the donor from the camera, to detect a reaction of the donor to the blood collection procedure based on the image, wherein the reaction is detected by comparing the image data to a predetermined threshold to detect a donor condition, to retrieve from a memory an instruction relating to the condition of the donor, and to display the instruction relating to the donor on the display, wherein the instruction assists the operator in how to respond to the detected donor condition.

17. The system of claim 16, wherein the wireless transceiver is configured to communicate with the blood collection device to provide a notification relating to the condition of the patient to the blood collection device.

18. The device of claim 1, wherein the processing circuit is configured to receive the input data from the blood collection device.

19. The device of claim 16, wherein the reaction detected by the processing circuit is at least one of facial flushing or an allergy symptom, and wherein the instruction is an instruction for how to safely shut down the blood collection procedure.

* * * * *